(12) United States Patent
Palmaz et al.

(10) Patent No.: US 8,728,563 B2
(45) Date of Patent: May 20, 2014

(54) ENDOLUMINAL IMPLANTABLE SURFACES, STENTS, AND GRAFTS AND METHOD OF MAKING SAME

(75) Inventors: Julio C. Palmaz, Napa, CA (US); Armando Garza, San Jose, CA (US)

(73) Assignee: Palmaz Scientific, Inc., Dallas, TX (US)

( * ) Notice: Subject to any disclaimer, the term of this patent is extended or adjusted under 35 U.S.C. 154(b) by 0 days.

(21) Appl. No.: 13/099,980

(22) Filed: May 3, 2011

(65) Prior Publication Data
US 2012/0282391 A1 Nov. 8, 2012

(51) Int. Cl.
*A61F 2/06* (2013.01)
*B05D 3/12* (2006.01)
*B05D 5/10* (2006.01)
*B32B 1/08* (2006.01)
*B44C 1/22* (2006.01)

(52) U.S. Cl.
USPC .......... 427/2.24; 427/2.25; 427/256; 427/265; 216/8; 216/28; 216/32; 216/41; 216/49; 216/65; 216/75; 623/1.42; 623/1.46

(58) Field of Classification Search
USPC .............. 427/2.1, 2.24, 2.25, 256, 265; 216/8, 216/28, 32, 41, 49, 65, 75; 623/1.42–1.48
See application file for complete search history.

(56) References Cited

U.S. PATENT DOCUMENTS

| | | | |
|---|---|---|---|
| 4,425,696 A | 1/1984 | Torniainen | 29/157.3 |
| 4,437,327 A | 3/1984 | Madden | 72/94 |
| 4,657,544 A | 4/1987 | Pinchuk | 623/1 |
| 4,733,665 A | 3/1988 | Palmaz | 128/343 |
| 5,102,417 A | 4/1992 | Palmaz | 606/195 |
| 5,133,845 A | 7/1992 | Vallana et al. | 204/192.15 |
| 5,195,984 A | 3/1993 | Schatz | 606/195 |
| 5,207,709 A | 5/1993 | Picha | 623/11 |
| 5,278,063 A | 1/1994 | Hubbell et al. | 435/240.243 |
| 5,370,684 A | 12/1994 | Vallana et al. | 623/1 |
| 5,387,247 A | 2/1995 | Vallana et al. | 623/66 |
| 5,423,885 A | 6/1995 | Williams | 623/1 |
| 5,510,628 A | 4/1996 | Georger, Jr. et al. | 257/32 |
| 5,607,463 A | 3/1997 | Schwartz et al. | 623/1 |
| 5,649,951 A | 7/1997 | Davidson | 606/198 |

(Continued)

FOREIGN PATENT DOCUMENTS

| | | | | |
|---|---|---|---|---|
| EP | 0 603 959 | 6/1994 | | A61F 2/06 |
| EP | 0 701 803 | 3/1996 | | A61F 2/30 |

(Continued)

OTHER PUBLICATIONS

Miller et al. Laser Micromachining for biomedical applications. JOM Journal of the Minerals, Metals and Materials Society vol. 61, No. 9 (2009), 35-40.*

(Continued)

*Primary Examiner* — Cachet Sellman
(74) *Attorney, Agent, or Firm* — J. Peter Paredes; Rosenbaum IP

(57) ABSTRACT

A method of manufacturing an endoluminal implantable surface, stent, or graft includes the steps of providing an endoluminal implantable surface, stent, or graft having an inner wall surface, an outer wall surface, and a wall thickness and forming a pattern design into the endoluminal implantable surface, stent, or graft. At least one groove is created in the inner surface of the intravascular stent by applying a laser machining method to the inner surface.

12 Claims, 15 Drawing Sheets

FIG. 2

(56) References Cited

U.S. PATENT DOCUMENTS

| | | | |
|---|---|---|---|
| 5,690,670 A | 11/1997 | Davidson | 606/198 |
| 5,725,573 A | 3/1998 | Dearnaley et al. | 623/2 |
| 5,733,303 A | 3/1998 | Israel et al. | 606/198 |
| 5,735,896 A | 4/1998 | Amon et al. | 623/1 |
| 5,772,864 A | 6/1998 | Moller | 205/73 |
| 5,782,908 A | 7/1998 | Cahalan et al. | 623/1 |
| 5,843,289 A | 12/1998 | Lee et al. | 204/192.3 |
| 5,855,802 A | 1/1999 | Acciai et al. | 216/8 |
| 5,891,507 A | 4/1999 | Jayaraman | 427/2.25 |
| 5,895,419 A | 4/1999 | Tweden et al. | 623/2 |
| 5,897,911 A | 4/1999 | Loeffler | 427/2.25 |
| 5,932,299 A | 8/1999 | Katoot | 427/508 |
| 5,955,588 A | 9/1999 | Tsang et al. | 536/21 |
| 6,001,622 A | 12/1999 | Dedhar et al. | 435/194 |
| 6,027,526 A | 2/2000 | Limon et al. | 623/1 |
| 6,077,413 A | 6/2000 | Hafeli et al. | 205/170 |
| 6,086,773 A | 7/2000 | Dufresne et al. | 216/8 |
| 6,096,175 A * | 8/2000 | Roth | 204/192.15 |
| 6,103,320 A | 8/2000 | Matsumoto et al. | 427/535 |
| 6,140,127 A | 10/2000 | Sprague | 435/395 |
| 6,143,370 A | 11/2000 | Panagiotou et al. | 427/422 |
| RE36,991 E | 12/2000 | Yamamoto et al. | 204/403 |
| 6,183,255 B1 | 2/2001 | Oshida | 433/201.1 |
| 6,190,404 B1 | 2/2001 | Palmaz et al. | 623/1.15 |
| 6,192,944 B1 | 2/2001 | Greenhalgh | 139/425 R |
| 6,207,536 B1 | 3/2001 | Matsumoto et al. | 438/478 |
| 6,217,607 B1 * | 4/2001 | Alt | 623/1.1 |
| 6,253,441 B1 | 7/2001 | Wheat et al. | 29/527.2 |
| 6,258,121 B1 | 7/2001 | Yang et al. | 623/1.46 |
| 6,274,014 B1 | 8/2001 | Matsumoto et al. | 204/298.11 |
| 6,280,467 B1 | 8/2001 | Leonhardt | 623/1.16 |
| 6,325,825 B1 | 12/2001 | Kula et al. | 623/1.3 |
| 6,334,868 B1 | 1/2002 | Ham | 623/1.13 |
| 6,379,383 B1 | 4/2002 | Palmaz et al. | 623/1.49 |
| 6,432,128 B1 | 8/2002 | Wallace et al. | 623/1.11 |
| 6,514,261 B1 | 2/2003 | Randall et al. | 606/108 |
| 6,520,923 B1 | 2/2003 | Jalisi | 600/585 |
| 6,527,919 B1 | 3/2003 | Roth | 204/192.15 |
| 6,527,938 B2 | 3/2003 | Bales et al. | 205/229 |
| 6,533,905 B2 * | 3/2003 | Johnson et al. | 204/192.15 |
| 6,537,310 B1 * | 3/2003 | Palmaz et al. | 623/1.13 |
| 6,652,579 B1 | 11/2003 | Cox et al. | 623/1.34 |
| 6,689,473 B2 | 2/2004 | Guire et al. | 428/412 |
| 6,726,829 B2 * | 4/2004 | Trozera | 205/655 |
| 6,849,085 B2 | 2/2005 | Marton | 623/1.13 |
| 7,354,519 B1 * | 4/2008 | Fank et al. | 216/8 |
| 7,574,799 B2 * | 8/2009 | Stinson | 29/896.6 |
| 7,575,593 B2 * | 8/2009 | Rea et al. | 623/1.42 |
| 8,037,733 B2 | 10/2011 | Banas et al. | 72/370.04 |
| 2001/0001834 A1 | 5/2001 | Palmaz et al. | 623/1.15 |
| 2001/0039454 A1 | 11/2001 | Ricci et al. | 623/23.5 |
| 2002/0016623 A1 | 2/2002 | Kula et al. | 623/1.11 |
| 2002/0017503 A1 * | 2/2002 | Banas et al. | 219/69.11 |
| 2002/0156522 A1 | 10/2002 | Ivancev et al. | 623/1.15 |
| 2002/0193869 A1 | 12/2002 | Dang | 623/1.15 |
| 2003/0028246 A1 | 2/2003 | Palmaz et al. | 623/1.49 |
| 2003/0093141 A1 | 5/2003 | Dimatteo et al. | 623/1.13 |
| 2003/0130718 A1 | 7/2003 | Palmas et al. | 623/1.12 |
| 2003/0139801 A1 * | 7/2003 | Sirhan et al. | 623/1.15 |
| 2004/0014253 A1 | 1/2004 | Gupta et al. | 438/48 |
| 2004/0226922 A1 | 11/2004 | Flanagan | 219/121.64 |
| 2005/0055085 A1 | 3/2005 | Rivron et al. | 623/1.39 |
| 2005/0102036 A1 | 5/2005 | Bartee et al. | 623/23.76 |
| 2005/0119723 A1 | 6/2005 | Peacock, III | 623/1.15 |
| 2005/0180919 A1 * | 8/2005 | Tedeschi | 424/9.4 |
| 2006/0178751 A1 | 8/2006 | Despres, III et al. | 623/23.5 |
| 2007/0088430 A1 | 4/2007 | Banas et al. | 623/1.16 |
| 2007/0225823 A1 | 9/2007 | Hawkins et al. | 623/23.51 |
| 2008/0071355 A1 * | 3/2008 | Weber et al. | 623/1.16 |
| 2008/0183276 A1 | 7/2008 | Melder | 623/1.15 |
| 2009/0018645 A1 | 1/2009 | Cambronne et al. | 623/1.34 |
| 2010/0305682 A1 | 12/2010 | Furst | 623/1.13 |

FOREIGN PATENT DOCUMENTS

| | | | |
|---|---|---|---|
| EP | 0 734 699 | 11/1996 | A61F 2/06 |
| EP | 0 815 806 | 1/1998 | A61F 2/06 |
| EP | 0 850 604 | 1/1998 | A61F 2/06 |
| EP | 0 974 314 | 1/2000 | A61F 2/06 |
| EP | 1 028 672 | 6/2005 | A61F 2/06 |
| JP | 07-284527 | 10/1995 | A61F 27/00 |
| JP | 09-225021 | 9/1997 | A61L 27/00 |
| JP | 63-502405 | 9/1998 | A61L 33/00 |
| JP | 2001-294411 | 10/2001 | C01B 25/32 |
| JP | 2002-017847 | 1/2002 | A61L 27/00 |
| WO | WO95/12472 | 5/1995 | B23K 26/02 |
| WO | WO98/45506 | 10/1998 | C25D 7/04 |
| WO | WO99/23977 | 5/1999 | A61F 2/06 |
| WO | WO00/10623 | 3/2000 | A61L 31/14 |
| WO | WO01/00112 | 1/2001 | A61F 2/06 |
| WO | WO01/35865 | 5/2001 | A61F 2/06 |
| WO | WO01/68158 | 9/2001 | A61L 27/08 |
| WO | WO01/74274 | 10/2001 | A61F 2/06 |
| WO | WO01/76525 | 10/2001 | A61F 2/06 |
| WO | WO01/87371 | 11/2001 | A61L 27/42 |
| WO | WO01/89420 | 11/2001 | A61F 2/06 |
| WO | WO02/38080 | 5/2002 | A61F 2/00 |

OTHER PUBLICATIONS

Calmar Laser, Inc., Application of fiber laser chirped pulse amplifiers (Application notes) PN 200-0400-00, Rev 1.0: pp. 1-9 (2009).

Chen, C., et al., "Reports: Geometric Control of Cell Life and Death" *Science* 276(5317): 1425-1428 (1997).

Chu, P.K., "Plasma-surface modification of biomaterials" *Materials Science and Engineering* R 36: 143-206 (2002).

Davies, P.F., et al., "Endothelial cell adhesion in real time" The Journal of Clinical Investigation 91: 2640-2652 (1993).

Davies, P.F., et al., "Quantitative studies of endothelial cell adhesion" *The Journal of Clinical Investigation*, 93: 2031-2038 (1994).

Den Braber, E.T., et al., "Effects of parallel surface microgrooves and surface energy on cell growth" *Journal of Biomedical Materials Research* 29: 511-518 (1995).

Giancotti, F.G., et al., "Review integrin signaling" Science 285(5430): 1028-1032 (1999).

Hehrlein, C., et al., "Therapy and prevention: Influence of surface texture and charge on the biocompatibility of endovascular stents" *University of Heidelberg, Germany; Dept. of Cardiology, Antatomy and Physical Chemistry*, pp. 581-585 (1995).

Holleck, H., et al., "Multilayer PVD coatings for wear protection" *Surface and Coatings Technology* 76-77(1): 328-336 (1997) Abstract Only.

Kasemo, B., "Biomaterial and implant surfaces: On the role of cleanliness, contamination, and preparation procedures" J. Biomed. Mater Res.: Applied Biomaterials 22(A2): 145-158 (1988).

Kasemo, B., "Biological surface science" *Surface Science* 500: 656-677 (2002).

Kazmierska, K., et al., "Bioactive coatings for minimally invasive medical devices: Surface modification in the service of medicine" *Recent Patents on Biomedical Engineering* 2: 1-14 (2009).

Liang, C., et al., "Preparation of porous microstructures on NiTi alloy surface with femtosecond laser pulses" *Chinese Science Bulletin* 53(5): 700-705 (2008).

Liu, X., et al., "Surface modification of titanium, titanium alloys, and related materials for biomedical applications" *Materials Science and Engineering* R 47: 49-121 (2004).

Loh, I., "Plasma surface modification in biomedical applications" *AST Technical Journal*, pp. 1-6 (undated).

Matsuda, T., "Control of cell adhesion, migration and orientation on photochemically microprocessed surfaces" *Journal of Biomedical Materials Research* 32: 165-173.

Palmaz, J., et al., "New advances in endovascular technology" *Texas Heart Institute Journal* 24(3): 156-159 (1997).

Palmaz, J., et al., "Influence of stent design and material composition on procedure outcome" *Journal of Vascular Surgery* 36(5): 1031-1039 (2002).

(56) References Cited

OTHER PUBLICATIONS

Sprague, E., et al., "Electrostatic forces on the surface of metals as measured by atomic force microscopy" *J. Long Term Eff Med Implants*, 10(1-2): 111-125 (2000).

Raydiance, Inc., "Athermal ablation of nitinol for stent manufacturing" *Raydiance Application Spotlight* pp. 1-6 (2009).

Tanous, A.C., "Laser cutting takes the heat out of stent manufacturing" *Industrial Laser Solutions* pp. 20-23 (Jan./Feb. 2010).

Van der Giessen, W.J., et al., "Marked inflammatory sequel to implantation of biodegradable and nonbiodegradable polymers in porcine coronary arteries" *Circulation* 94(7): 1690-1697 (1996).

Zarbakhsh, A., "Characterization of photon-controlled titanium oxide surfaces" *ISIS Experimental Report*, Rutherford Appelton Laboratory, www.isis.rl.ac.uk/isis2001/reports/11144.pdf (2000).

Zheng, H.Y., et al., "Femtosecond laser processing of nitinol" *Applied Surface Science* 228 pp. 201-206 (2004).

Zheng, H.Y., et al., "Ultrashort pulse laser micromachined microchannels and their application in an optical switch" *Int J Adv Manuf Technol* 27: 925-929 (2006).

* cited by examiner

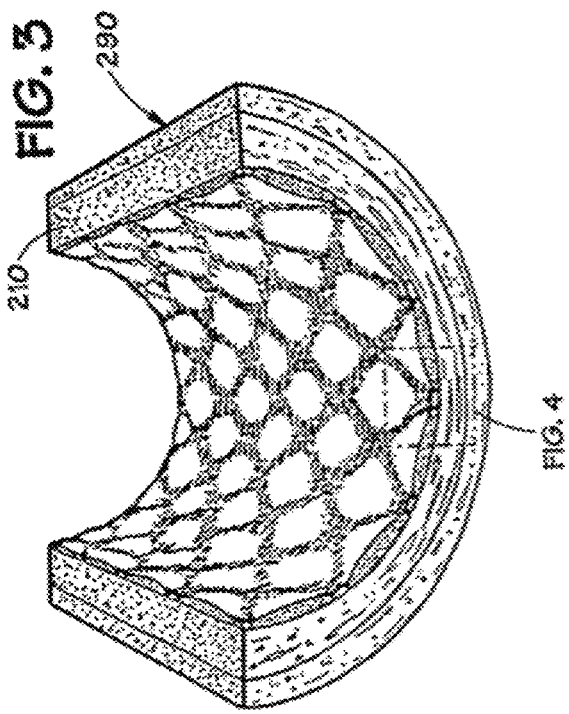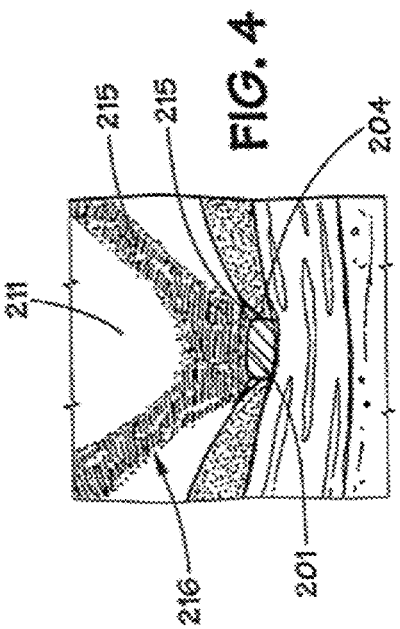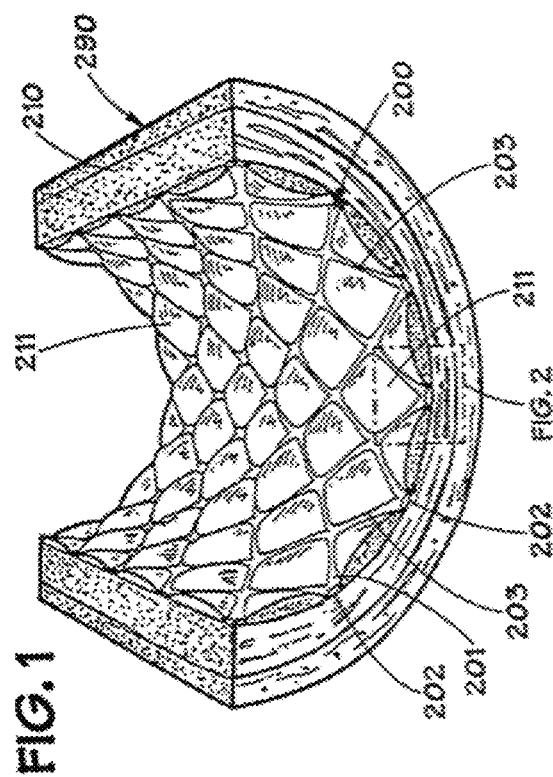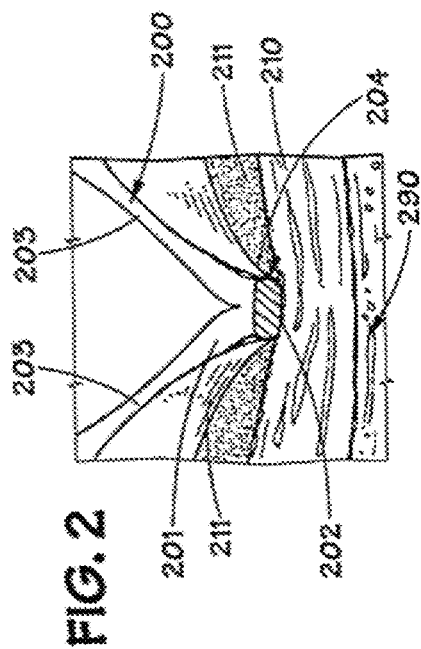

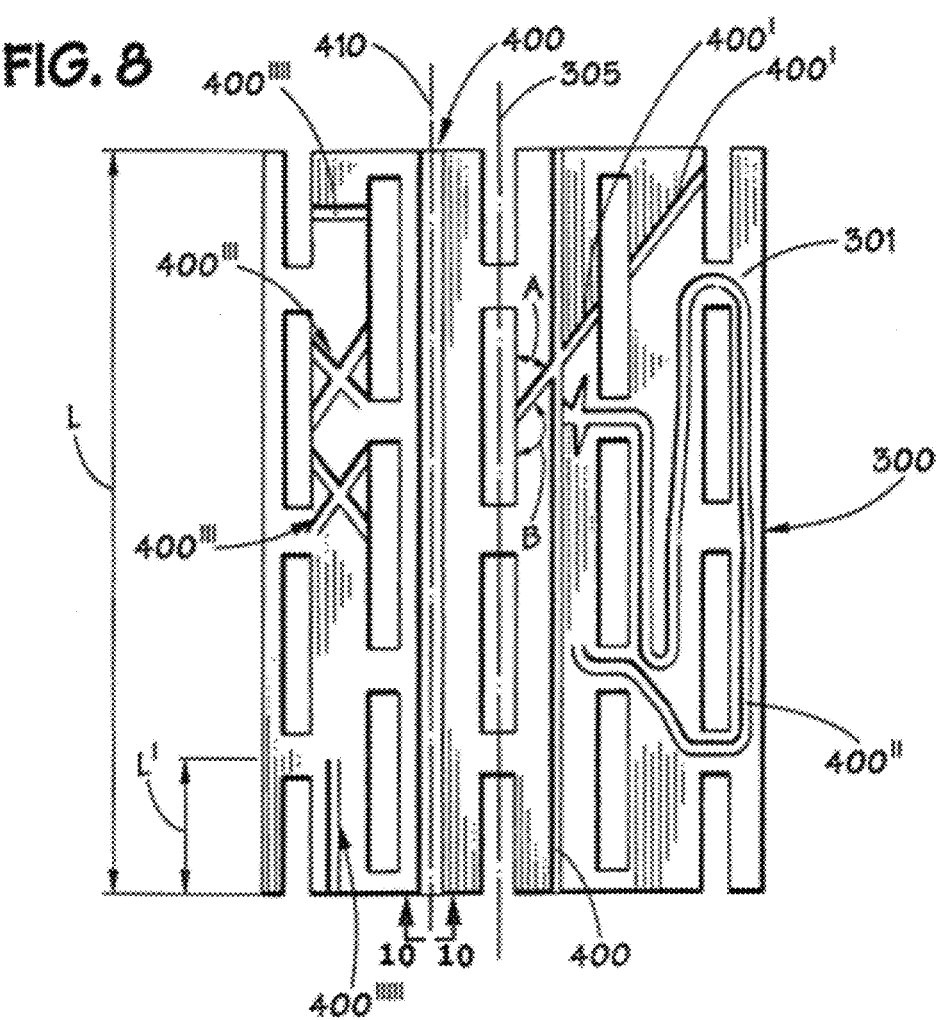

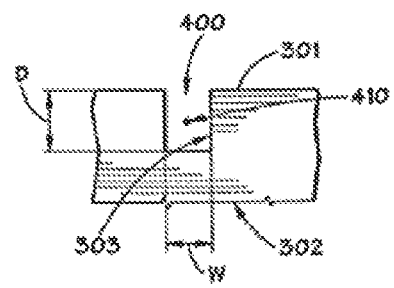
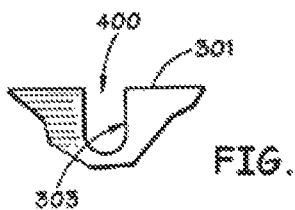
FIG. 10 FIG. 11
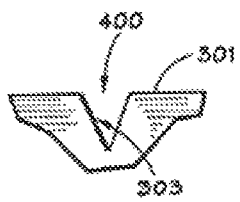
FIG. 12
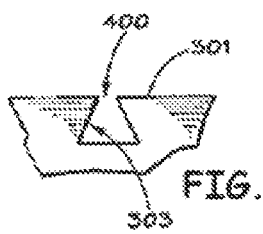
FIG. 13 FIG. 14
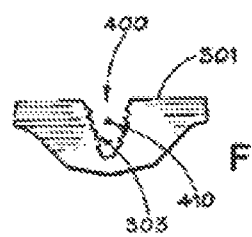
FIG. 15
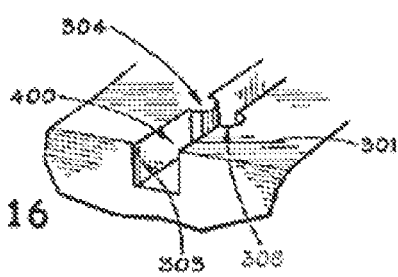
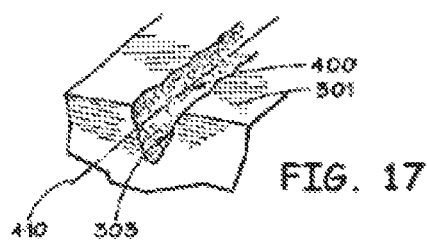
FIG. 16 FIG. 17

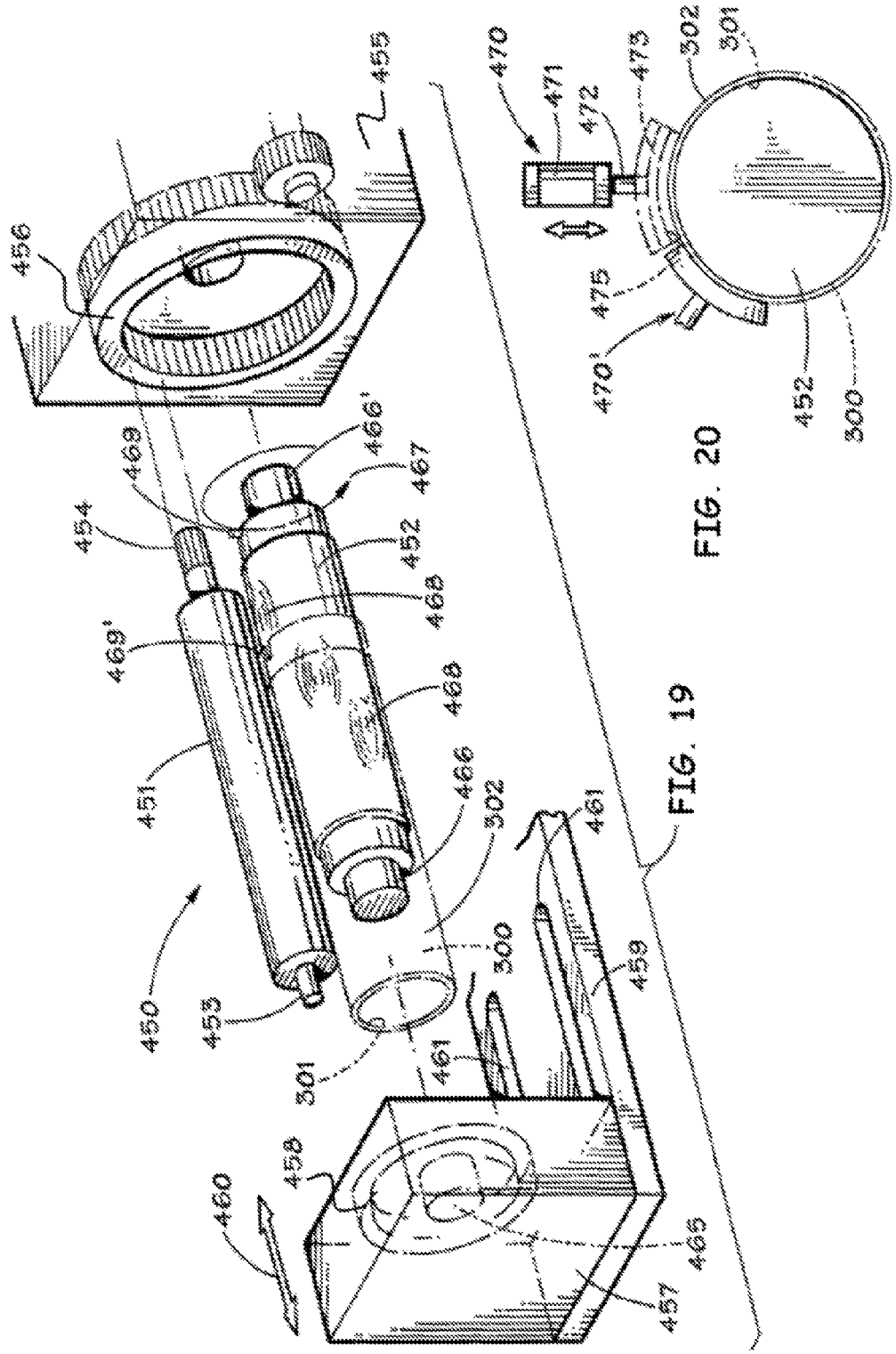

ENDOLUMINAL IMPLANTABLE SURFACES, STENTS, AND GRAFTS AND METHOD OF MAKING SAME

BACKGROUND OF THE INVENTION

The invention relates to methods and apparatus for manufacturing intravascular stents, wherein the intravascular stent has an inner surface treated to promote the migration of endothelial cells onto the inner surface of the intravascular stent.

Intravascular stents are used, in general, as a mechanical means to solve the most common problems of percutaneous balloon angioplasty, such as elastic recoil and intimal dissection. One problem intra-luminal stent placement shares with other revascularization procedures, including bypass surgery and balloon angioplasty, is restenosis of the artery. An important factor contributing to this possible reocclusion at the site of stent placement is injury to, and loss of, the natural non-thrombogenic lining of the arterial lumen, the endothelium. Loss of the endothelium, exposing the thrombogenic arterial wall matrix proteins, along with the generally thrombogenic nature of prosthetic materials, initiates platelet deposition and activation of the coagulation cascade. Depending on a multitude of factors, such as activity of the fibrinolytic system, the use of anticoagulants, and the nature of the lesion substrate, the result of this process may range from a small mural to an occlusive thrombus. Secondly, loss of the endothelium at the interventional site may be critical to the development and extent of eventual intimal hyperplasia at the site.

Previous studies have demonstrated that the presence of an intact endothelial layer at an injured arterial site can significantly inhibit the extent of smooth muscle cell-related intimal hyperplasia. Rapid re-endothelialization of the arterial wall, as well as endothelialization of the prosthetic surface, or inner surface of the stent, are therefore critical for the prevention of low-flow thrombosis and for continued patency. Unless endothelial cells from another source are somehow introduced and seeded at the site, coverage of an injured area of endothelium is achieved primarily, at least initially, by migration of endothelial cells from adjacent arterial areas of intact endothelium.

Although an in vitro biological coating to a stent in the form of seeded endothelial cells on metal stents has been previously proposed, there are believed to be serious logistic problems related to live-cell seeding, which may prove to be insurmountable. Thus, it would be advantageous to increase the rate at which endothelial cells from adjacent arterial areas of intact endothelium migrate upon the inner surface of the stent exposed to the flow of blood through the artery. At present, most intravascular stents are manufactured of stainless steel and such stents become embedded in the arterial wall by tissue growth weeks to months after placement. This favorable outcome occurs consistently with any stent design, provided it has a reasonably low metal surface and does not obstruct the fluid, or blood, flow through the artery. Furthermore, because of the fluid dynamics along the inner arterial walls caused by blood pumping through the arteries, along with the blood/endothelium interface itself, it has been desired that the stents have a very smooth surface to facilitate migration of endothelial cells onto the surface of the stent. In fact, it has been reported that smoothness of the stent surface after expansion is crucial to the biocompatibility of a stent, and thus, any surface topography other than smooth is not desired. Christoph Hehriein, et al., Influence of Surface Texture and Charge On the Biocompatibility of Endovascular Stents, Coronary Artery Disease, Vol. 6, pages 581-586 (1995).

After the stent has been coated with serum proteins, the endothelium grows over the fibrin-coated metal surface on the inner surface of the stent until a continuous endothelial layer covers the stent surface, in days to weeks. Endothelium renders the thrombogenic metal surface protected from thrombus deposition, which is likely to form with slow or turbulent flow. At present, all intravascular stents made of stainless steel, or other alloys or metals, are provided with an extremely smooth surface finish, such as is usually obtained by electropolishing the metallic stent surfaces. Although presently known intravascular stents, including the Palmaz™ and Palmaz-Schatz™ balloon-expandable stents, have been demonstrated to be successful in the treatment of coronary disease as an adjunct to balloon angioplasty, intravascular stents could be even more successful and efficacious if the rate and/or speed of endothelial cell migration onto the inner surface of the stent could be increased. Accordingly, the present invention attempts to solve these problems, as well as others.

SUMMARY OF THE INVENTION

In one embodiment, a method of manufacturing an endoluminal implantable surface is presented. The method includes the steps of providing an endoluminal implantable surface, stent, or graft having an inner wall surface, an outer wall surface, and a wall thickness between about 5 and about 75 microns, alternatively between about 10 and 60 microns, and forming a pattern design into the endoluminal implantable surface, stent, or graft. The method further includes the step of creating at least one groove in the inner surface of the intravascular stent by applying a laser machining method to the inner surface.

In another embodiment, a method of manufacturing an endoluminal implantable surface is presented. The method includes the steps of providing an endoluminal implantable surface, stent, or graft having an inner wall surface and an outer wall surface, and forming a pattern design into the endoluminal implantable surface, stent, or graft. The method further includes the steps of pre-structuring at least one of the inner wall and the outer wall surfaces by applying a laser machining method to the at least one wall surface to create an image of a desired pattern, and vacuum depositing material over the image of the desired pattern to create a patterned surface overlying the at least one surface and including the desired pattern. A wall thickness including the patterned surface overlying the at least one surface measures between about 5 and about 75 microns, alternatively between about 10 and 60 microns.

In a further embodiment, a method of manufacturing an endoluminal implantable surface, stent, or graft is presented. The method includes the steps of providing an endoluminal implantable surface, stent, or graft having an inner wall surface and an outer wall surface, and forming a pattern design into the endoluminal implantable surface, stent, or graft. The method further includes the steps of pre-structuring at least one of the inner wall and the outer wall surfaces by applying a photolithographic method to the at least one wall surface to create an image of a desired pattern, and vacuum depositing material over the image of the desired pattern to create a patterned surface overlying the at least one surface and including the desired pattern. A wall thickness including the patterned surface overlying the at least one surface measures between about 5 and about 75 microns.

The methods for manufacturing intravascular stents and apparatuses thereof, when compared with presently known methods for manufacturing such stents, increase the rate of migration of endothelial cells upon the inner surface of the intravascular stent.

BRIEF DESCRIPTION OF THE FIGURES

FIG. 1 is a partial cross sectional perspective view of a portion of an intravascular stent embedded within an arterial wall of a patient.

FIG. 2 is an exploded view of the outlined portion of FIG. 1 denoted as FIG. 2.

FIG. 3 is a partial cross-sectional, perspective view corresponding to FIG. 1 after the passage of time.

FIG. 4 is an exploded view of the outlined portion of FIG. 3 denoted as FIG. 4.

FIG. 8 is a plan view of an interior portion of an unexpanded intravascular stent in accordance with one embodiment.

FIGS. 10-17 are various embodiments of an exploded view of a groove taken along line 10-10 of FIG. 8, illustrating various cross-sectional configurations and characteristics of various embodiments of grooves in accordance with one embodiment.

FIG. 19 is an exploded perspective view of a calendaring apparatus for manufacturing stents in accordance with one embodiment.

FIG. 20 is a partial cross-sectional view of a stamping apparatus for manufacturing stents in accordance with one embodiment, looking down the longitudinal axis of a mandrel;

DETAILED DESCRIPTION OF THE PREFERRED EMBODIMENTS

Figure 5:
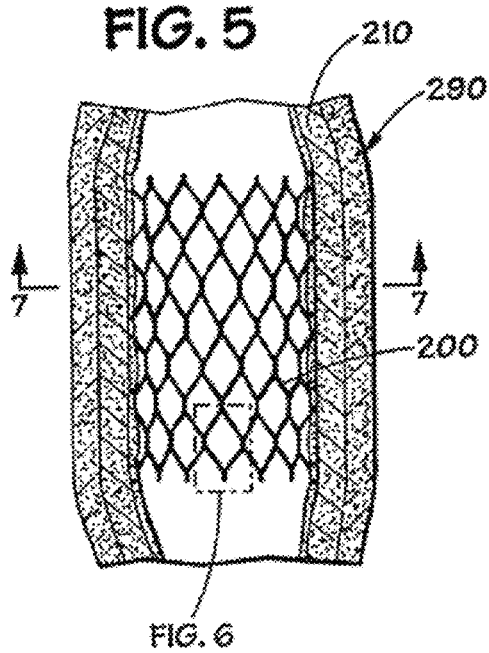
FIG. 5 is a partial cross-sectional view of the stent and artery of FIGS. 1 and 3 after a further passage of time.

With reference to FIGS. 1 and 2, an intravascular stent 200 is illustrated being disposed within an artery 290 in engagement with arterial wall 210. For illustrative purposes only, intravascular stent 200, shown in FIGS. 1-6 is a Palmaz™ balloon-expandable stent, as is known in the art, stent 200 having an inner surface 201 and an outer surface 202. FIGS. 1 and 2 illustrate stent 200 shortly after it has been placed within artery 290, and after stent 200 has been embedded into arterial wall 210, as is known in the art. FIGS. 1 and 2 illustrate what may be generally characterized as correct placement of an intravascular stent. Stent 200 preferably includes a plurality of metal members, or struts, 203, which may be manufactured of stainless steel, or other metal materials, as is known in the art. As illustrated in FIGS. 1 and 2, correct placement of stent 200 results in tissue mounds 211 protruding between the struts 203, after struts 203 have been embedded in the arterial wall 210. Struts 203 also form troughs, or linear depressions, 204 in arterial wall 210. Dependent upon the degree of blockage of artery 290, and the type and amount of instrumentation utilized prior to placement of stent 200, the mounds of tissue 211 may retain endothelial cells (not shown).

With reference to FIGS. 3 and 4, after the passage of time, a thin layer of thrombus 215 rapidly fills the depressions 204, and covers the inner surfaces 201 of stent 200. As seen in FIG. 4, the edges 216 of thrombus 215 feather toward the tissue mounds 211 protruding between the struts 203. The endothelial cells which were retained on tissue mounds 211 can provide for reendothelialization of arterial wall 210.

Figure 6:
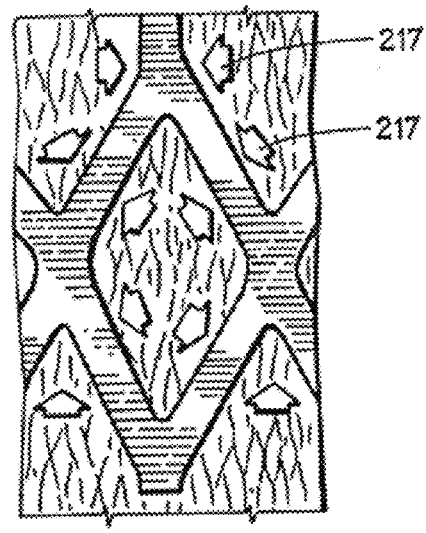
FIG. 6 is an exploded view of the outlined portion of FIG. 5 denoted as FIG. 6.
Figure 7:
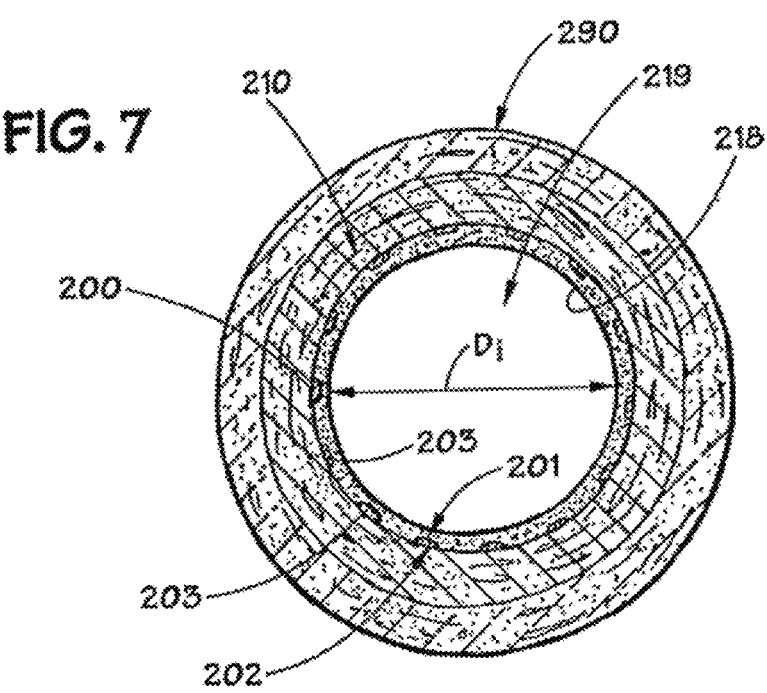
FIG. 7 is a partial cross-sectional view of the stent and artery of FIG. 5, taken along lines 7-7 of FIG. 5, and illustrates rapid endothelialization resulting in a thin neointimal layer covering the stent.

With reference to FIGS. 5 and 6, endothelial regeneration of artery wall 210 proceeds in a multicentric fashion, as illustrated by arrows 217, with the endothelial cells migrating to, and over, the struts 203 of stent 200 covered by thrombus 215. Assuming that the stent 200 has been properly implanted, or placed, as illustrated in FIGS. 1 and 2, the satisfactory, rapid endothelialization results in a thin tissue layer 218, as shown in FIG. 7. As is known in the art, to attain proper placement, or embedding, of stent 200, stent 200 must be slightly overexpanded. In the case of stent 200, which is a balloon-expandable stent, the balloon diameter chosen for the final expansion of stent 200 must be 10% to 15% larger than the matched diameter of the artery, or vessel, adjacent the site of implantation. As shown in FIG. 7, the diameter Di of the lumen 219 of artery 290 is satisfactory. If the reendothelialization of artery wall 210 is impaired by underexpansion of the stent or by excessive denudation of the arterial wall prior to, or during, stent placement, slower reendothelialization occurs. This results in increased thrombus deposition, proliferation of muscle cells, and a decreased luminal diameter Di, due to the formation of a thicker neointimal layer.

With reference to FIG. 8, an intravascular stent 300 in accordance with one embodiment is illustrated. The intravascular stent, or stent, 300 has an inner surface 301, and an outer surface 302, outer surface 302 (See FIG. 1) normally being embedded into the arterial wall 210 (See FIGS. 1-3, 5, and 7) in an abutting relationship. For illustrative purposes only, the structure of the intravascular stent 300 is illustrated as being a Palmaz™ balloon-expandable stent, as is known in the art, illustrated in its initial, unexpanded configuration. It should be understood that the improvement of one embodiment is believed to be suitable for use with any intravascular stent, stent-grafts, grafts, heart valves, venous valves, filters, occlusion devices, catheters, osteal implants, implantable contraceptives, implantable antitumor pellets or rods, or other implantable medical devices having any construction or made of any material as will be hereinafter described. Similarly, the improvement of the embodiments for the methods for manufacturing intravascular stents is also believed to be applicable to the manufacturing of any type of intravascular medical device, stent-grafts, grafts, heart valves, venous valves, filters, occlusion devices, catheters, osteal implants, implantable contraceptives, implantable antitumor pellets or rods, or other implantable medical devices, as will also be hereinafter described.

Figure 9A:
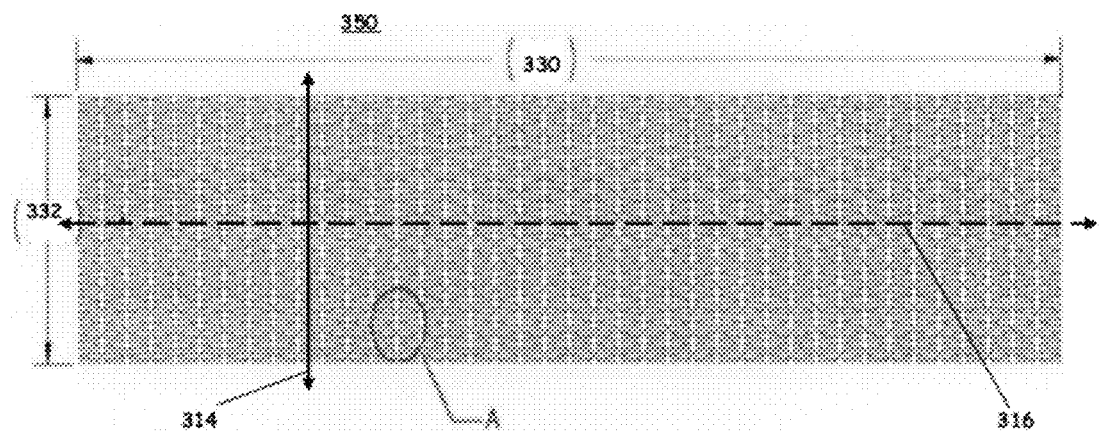
FIG. 9A is a side view of an embodiment of an intravascular stent.
Figure 9B:
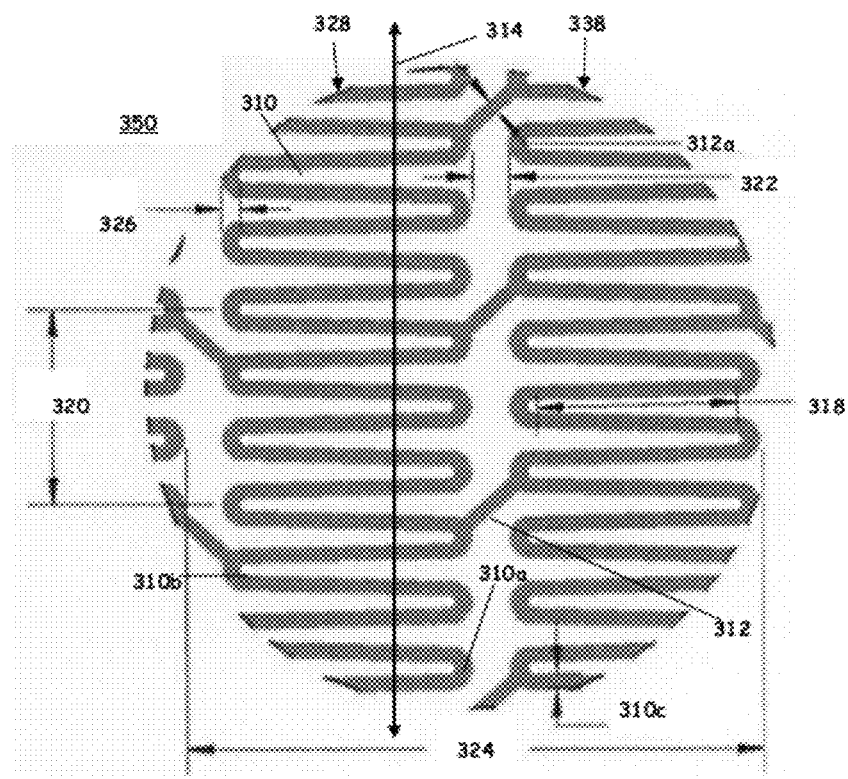
FIG. 9B is an enlarged view of region A in FIG. 9A.

Referring to FIGS. 9A and 9B, in a preferred embodiment, an intravascular stent 350 consists generally of a tubular cylindrical element having a stent wall that defines the inner surface 301 and the outer surface 302 of the stent 350. The stent wall includes a wall thickness measured between the inner surface 301 and the outer surface 302. In one embodiment, the wall thickness includes at least one vacuum deposited layer of material. First structural elements 310 are distributed about the circumferential axis 314 of the stent 350 and extend generally parallel to the longitudinal axis 316 of the stent 350. The first structural elements 310 are connected as described hereinbelow to a plurality 328 of the first structural elements 310. Another plurality 338 of the first structural elements 310 is disposed longitudinally adjacent to the plurality 328 of the first structural elements 310. A plurality of second structural elements 312 interconnects adjacent pairs of the pluralities of the first structural elements 310, for example, the pluralities 328, 338 of the first structural elements 310.

In this embodiment, each plurality of the first structural elements 310 has a generally sinusoidal configuration with a plurality of peaks 310a and a plurality of troughs 310b disposed between adjacent first structural elements 310. The plurality of peaks 310a and the plurality of troughs 310b may have either regular or irregular periodicity along the circumferential axis 314 of each of the pluralities of the first structural elements 310. Further, the plurality of peaks 310a and the plurality of troughs 310b may have either regular or irregular periodicity longitudinally along the pluralities of the first structural elements 310, for example, longitudinally along the pluralities 328, 338, etc.

Alternatively, each of the pluralities of the first structural elements 310 may have regions of regular periodicity and regions of irregular periodicity along the circumferential axis 314 thereof or longitudinally along the pluralities of the first structural elements 310, for example, longitudinally along the pluralities 328, 338, etc. In this embodiment, each of the plurality of second structural elements 312 preferably comprise linear elements which interconnect a peak 310a disposed between a pair of the first structural elements 310 on a first plurality, for example, the plurality 328 of the first structural elements 310, with a trough 310b disposed between a pair of the first structural elements 310 on an adjacent plurality, for example the plurality 338 of the first structural elements 310. In other embodiments, the first and second structural elements 310, 312 may have shapes and/or configurations different from those described hereinabove with regard to FIGS. 9A and 9B, as desired, appropriate, or suitable for a particular application.

The intravascular stent 300, 350 including the first and second structural elements 310, 312 are preferably made of materials chosen for their biocompatibility, material properties, i.e., tensile strength, yield strength, and their ease of deposition. Suitable materials include those selected from the group of materials consisting of elemental titanium, vanadium, aluminum, nickel, tantalum, zirconium, chromium, silver, gold, silicon, magnesium, niobium, scandium, platinum, cobalt, palladium, manganese, molybdenum, and alloys thereof, such as zirconium-titanium alloys, nitinol, and stainless steel.

Each of the first and second structural elements 310, 312 may be made of the same material or of different materials and have the same material properties or have different material properties. The term material properties is intended to encompass physical properties, including by way of example and not limitation, elasticity, tensile strength, mechanical properties, hardness, bulk and/or surface grain size, grain composition, grain boundary size, and intra- and inter-granular precipitates.

Similarly, the materials selected for the first structural elements 310 and the second structural elements 312 may be selected to have the same or different chemical properties. The term chemical properties is intended to encompass both any chemical reaction and change of state that the material may undergo after being implanted into a body and the physiological response of the body to the material after implantation.

The intravascular stent 300, 350 is preferably made of a material having controlled heterogeneities on the inner surface 301 thereof. As described in commonly assigned U.S. Pat. No. 6,379,383, issued Apr. 30, 2002, which is hereby incorporated by reference, heterogeneities are controlled by fabricating the material of the stent to have defined bulk and/or surface grain size, grain composition, grain boundary size, and chemical and intra- and inter-granular precipitates. The controlled heterogeneities allow for heightened laser machining techniques on the surface of the deposited film, whereby the surface of the deposited film allows for a decrease in heat-affected zones, slag, recast, and microstructure damages during laser machining.

The characteristically desirable material properties of the intravascular stent are: (a) optimum mechanical properties consistent with or exceeding regulatory approval criteria, (b) minimization of defects, such as cracking or pin hole defects, (c) a fatigue life of 400 million cycles as measured by simulated accelerated testing, (d) corrosion and/or corrosion-fatigue resistance, (e) biocompatibility without having biologically significant impurities in the material, (f) a substantially non-frictional abluminal surface to facilitate atraumatic vascular crossing and tracking with transcatheter techniques for stent introduction, (g) radiopaque at selected sites and MRI compatible, (h) have a luminal surface which is optimized for surface energy and microtopography, (i) minimal manufacturing and material cost consistent with achieving the desired material properties, and (j) high process yields.

The foregoing properties of the intravascular stent 300, 350 are achieved by employing vacuum deposition technologies such as vacuum deposition, ion-beam assisted evaporative deposition, and sputtering techniques. In ion-beam assisted evaporative deposition, it is preferable to employ dual and simultaneous thermal electron beam evaporation with simultaneous ion bombardment of the substrate using an inert gas, such as argon, xenon, nitrogen, or neon. Bombardment with an inert gas, such as argon, serves to reduce void content by increasing atomic packing density in the deposited material during deposition. The reduced void content in the deposited material allows the mechanical properties of that deposited material to be similar to the bulk material properties. Deposition rates of up to 20 nm/sec are achievable using ion beam assisted evaporative deposition techniques.

When sputtering techniques are employed, a 200-micron thick stainless steel film may be deposited within about four hours of deposition time. With the sputtering technique, it is preferable to employ a cylindrical sputtering target, a single circumferential source that concentrically surrounds the substrate that is held in a coaxial position within the source. Alternate deposition processes which may be employed to form the intravascular stent are cathodic arc and direct ion beam deposition. Planar magnetron sources or targets may also be employed. In diode sputtering, not all of the electrons escaping the target contribute to the ionized plasma glow area. The wasted electrons fly around the chamber causing radiation and other problems, for example, the heating of the target. A magnetron sputtering source addresses the electron problem by placing magnets behind, and sometimes, at the sides of the target. These magnets capture the escaping electrons and confine them to the immediate vicinity of the target. The ion current (density of ionized argon atoms hitting the target) is increased by an order of magnitude over conventional diode sputtering systems, resulting in faster deposition rates at lower pressure. The lower pressure in the chamber helps create a cleaner film. Target temperature is lower with magnetron sputtering enhancing the deposition of high quality films.

During vacuum deposition, the chamber pressure, the deposition pressure and the partial pressure of the process gases are controlled to optimize deposition of the desired species onto the substrate. Both the reactive and non-reactive gases are controlled and the inert or non-reactive gaseous species introduced into the deposition chamber are typically argon and nitrogen. The substrate may be either stationary or moveable, either rotated about its longitudinal axis, or moved longitudinally or radially relative to the longitudinal axis within the reactor to facilitate deposition of the material onto the substrate.

The material is vacuum deposited as a film or layer onto the substrate or onto a bulk material. The substrate may be a metal tubular substrate, a sacrificial metal tubular substrate, or a reusable ceramic or glass substrate. In one embodiment, the intravascular stent 300, 350 may comprise one or more layers of vacuum deposited material formed into a self-supporting structure. In another embodiment, the intravascular stent 300, 350 includes a bulk material, either a bulk material alone or a bulk material covered by one or more layers of vacuum deposited biocompatible material. Any number of layers of vacuum deposited material may be included as desired, appropriate, or suitable for a particular application.

Preferably, the wall thickness of the vacuum deposited metallic thin film is about 5 to about 75 μm, alternatively, between about 10 to about 60 μm. A sacrificial layer of a material, such as carbon or aluminum, may be deposited intermediate the substrate and the intravascular stent 300, 350. The sacrificial layer may be comprised of any coating that may be selectively dissolved or otherwise removed from the vacuum deposited metallic thin film via chemical, electrochemical, or mechanical means. In each of the preferred embodiments, the intravascular stent 300, 350 is fabricated by employing a vacuum deposition technique that entails vacuum depositing a stent-forming metal onto a substrate, wherein the wall thickness of the deposited stent-forming metal is about 5 to about 75 μm, alternatively, between about 10 to about 60 μm.

The one or more layers of vacuum deposited material may have thicknesses that are the same or different as desired or appropriate. Each layer may have a thickness in a range from about 1 nanometer to about 75 micrometers, from about 1 nanometer to about 20 micrometers, from about 1 nanometer to about 10 micrometers, from about 1 nanometer to about 5 micrometers, or from about 1 nanometer to about 3 micrometers.

The intravascular stent 300, 350 may be removed from the substrate after stent formation by any of a variety of methods. For example, the substrate may be removed by chemical means, such as etching or dissolution, by ablation, by machining, or by ultrasonic energy. Alternatively, the substrate may be removed by mechanical means due to differences in expansion coefficients of materials. The resulting intravascular stent 300, 350 may then be subjected to post-deposition processing to modify the crystalline structure, such as by annealing, or to modify the surface topography, such as by etching to affect and control heterogeneities on the luminal surface of the stent.

Incorporation of a stent pattern design can be accomplished using laser machining methods, including by way of example and not limitation, using a femto-second laser, using an excimer laser, using a Laser MicroJet (water assisted), laser assisted chemical machining, fiber laser chirped pulsed amplifiers, or other laser combinations. Photolithographic methods coupled with chemical, electrochemical, reactive ion etch (RIE) micro-machining techniques, as described hereinbelow with regard to FIGS. 25A-26B may be employed in-lieu of a laser machining method to machine stent pattern designs when appropriate. In one embodiment, the stent 300, 350 is patterned by a laser machining process or method employing a femto-second laser to create micron-sized structures without linear optical absorption of the material that can often lead to heat deposition, micro-cracks, and small collateral damage to the surrounding area. Laser assisted chemical machining may also include non-laser forms of light sources, such as superluminescent diodes (SLD), and the like. This technique can be described as photo-catalytic or photo-activated chemical machining using, for example, UV light as the catalyst to activate/initiate chemical reaction in exposed areas.

During an exemplary laser machining process, the intravascular stent 300, 350 may be held by a pneumatically controlled 3C collet system, with standard collet sizes ranging from 0.5 mm to 12 mm. A femto-second laser, for example, is used to cut the pattern design into the stent 300, 350. The exemplary femto-second laser operates at a wavelength of about 1552 nm, an energy per pulse of between about 10 and 100 μJ+/− about 5%, an average power of between about 2.5 watts to 15 watts or about 7.5 watts, a pulse width of less than about 1.0 picosecond (ps), typically between about 200-950 femtoseconds (fs), a peak power greater than about 50 MW, a pulse damage threshold between about 1-5 J/cm$^2$, no beam expansion, a beam diameter between about 4.5 mm+/−10% and a repetition rate of about 100 kHz to about 150 kHz. The material removal rate is approximately 30-50 nm/pulse and the maximum pulse rate is between 100 kHz-1 MHz with a uniformity of cut dimension of 1%.

Femtosecond lasers are lasers that emit optical pulses with aduration well below 1 ps (ultrashort pulses), i.e., in the domain of femtoseconds (1 fs=$10^{-15}$ s). Femtosecond lasers may include Bulk Lasers, Fiber Lasers, Dye Lasers, Semiconductor Lasers, titanium-sapphire lasers, and the like. Passively mode-locked solid-state bulk lasers can emit high-quality ultrashort pulses with typical durations between 30 fs and 30 ps. Various diode-pumped lasers, e.g. based on neodymium-doped or ytterbium-doped gain media, operate in this regime, with typical average output powers between 100 mW and 1 W. Titanium-sapphire lasers with advanced dispersion compensation are suitable for pulse durations below 10 fs and down to approximately 5 fs. The pulse repetition rate is between about 50 MHz and 500 MHz, even though there are low repetition rate versions with a few megahertz for higher pulse energies, and also miniature lasers with tens of gigahertz.

Various types of ultrafast fiber lasers, which are also in most cases passively mode-locked, typically offer pulse durations between about 50 and 500 fs, repetition rates between about 10 and 100 MHz, and average powers of a few milliwatts. Substantially higher average powers and pulse energies are possible, e.g. with stretched-pulse fiber lasers or with similar lasers, or in combination with a fiber amplifier. Dye lasers include a gain bandwidth that allows for pulse durations of the order of 10 fs, and different laser dyes are suitable for emission at various wavelengths, often in the visible spectral range. Some mode-locked diode lasers can generate pulses with femtosecond durations. Directly at the laser output, the pulses durations are usually at least several hundred femtoseconds, but with external pulse compression, much shorter pulse durations can be achieved. Vertical external-cavity surface-emitting lasers (VECSELs) can be passively mode-lock, which can deliver a combination of short pulse durations, high pulse repetition rates, and sometimes high average output power. Other types of femtosecond lasers are color center lasers and free electron lasers, where the latter can be made to emit femtosecond pulses even in the form of X-rays.

High precision, accurate, athermal cuts may be created on the stent 300, 350 using the femto-second laser. Such cuts are achieved by using a granite super structure, which provides excellent thermal expansion and vibration damping characteristics. A powdery residue results on the stent 300, 350 after laser machining with the exemplary femto-second laser. The residue is easily removed from the surface of the cut using ultrasonic agitation or similar means, which creates easy post-laser cleaning without the need to mechanically polish the stent 300, 350 or additional post-processing steps as indicated below.

Laser machining may be used to create features with high dimensional accuracy and precision in a vacuum deposited metallic stent, for example, the stent 300, 350, having a wall thickness in the range of about 5 to about 75 μm, alternatively, between about 10 and 60 μm. In one embodiment, the laser machining resolves 3 microns wide grooves using the femto-second laser, where the precision on the motion system is ±0.5 microns (X and Y-direction). Any of a variety of patterns may be laser cut into the stent 300, 350. Referring to FIG. 9B, by way of example and not limitation, the plurality 328 of the first structural elements 310 distributed about the circumferential axis 314 and having a generally sinusoidal configuration with a plurality of peaks 310a and troughs 310b may be formed using a laser machining method. Additionally, laser machining may be used to form the plurality of the second structural elements 312 interconnecting adjacent pairs of the pluralities of the first structural elements 310, as illustrated in FIG. 9B.

Figures 9C, 9D:
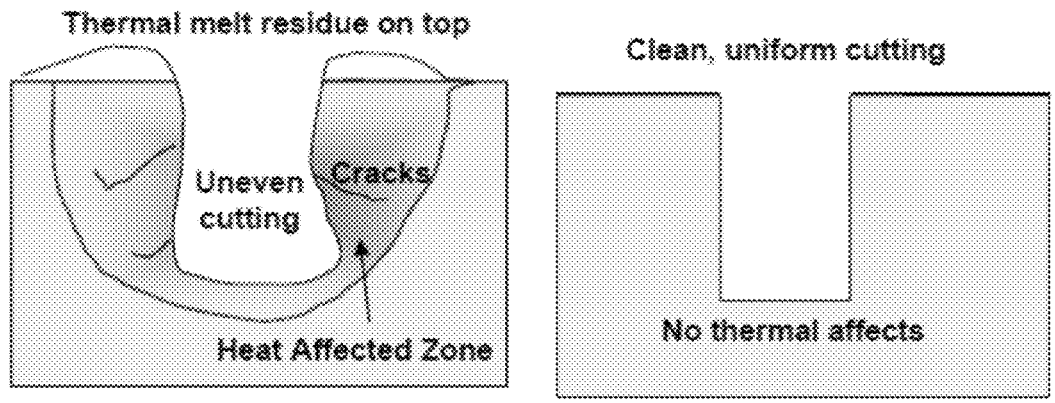
FIG. 9C is a schematic of the heat-affected zones due to long pulse laser machining.
FIG. 9D is a schematic of the femto-second laser machining without heat-affected zones.

The femto-second laser machines metal without leaving any appreciable amount of Heat-Affected Zones (HAZ) on the lateral surface, which is shown in FIG. 9C. The HAZ gives way to uneven cutting and cracks in the microstructure of the metal, which also leaves a thermal melt residue on the top surface. However, femto-second laser machines do not leave any HAZ or microstructure cracks due to the physics used by the femto-second lasers that results in athermal ablation, or cold ablation. After femto-second laser machining, a powdery residue results on the surface of the metal that is readily removed from the surface of the cut part using ultra-sonic agitation or similar means. The post-laser cleaning is without the need to mechanical polishing or processing, which is required with other lasers that leave a thermal melt residue on the top surface. The laser ablation features are clean and free of any slag or recast, as shown in FIG. 9D.

The grooves may be machined by the femto-second laser by using a focusing lens and altering the distance between the target and the workpiece, as such adjusting the focal position, adjusting the focal lens length, theoretical spot size or beam width, cutting speed, and power intensity of the laser. The focal position may be adjusted between about −2.5 to about 7 to alter the width of the groove or kerf width (depth of the groove or cut). The width of the groove may also be adjusted by moving the focal position closer to the surface of the metal and the width may be the narrowest when focused exactly on the surface of the sample. The depth of the grooves may be adjusted the laser beam is focused on the sample surface. The taper angle may be adjusted by focusing the beam on the top surface and adjusting the focal position between about −0.8 and +0.8, whereby the taper angle may be between about 45 and 90 degrees. The focal lens may be adjusted to be between about 20 and 200 mm. The power intensity may be adjusted between about 100 to 700 mW to provide wider grooves, increase the depths of grooves, or increase the aspect ratio of depth-to-width of the grooves. The depth may be increased by increasing the power intensity to be between about 100 nm and 70 μm. The theoretical spot size may be between approximately 5 and 100 μm, whereby the threshold-based ablation is able to produce features smaller than the spot size. As such, the measured kerf width of the groove may be between about 100 nm and 35 μm.

Continuous wave lasers ablate by way of a thermodynamic process of localized heating of the target lattice followed by a phase change or combustion. Femto-second pulsed lasers deliver tens of microJoules of energy between about 700-800 femtosecond pulses. When focused to a spot size from between about 30 microns down to the diffraction limit, ultrafast lasers generate high optical intensities. Preferably, ultrafast pulsed lasers include a pulse width T less than 5 picoseconds. Coupled with the high optical intensities is an electric field capable of initiating multi-photon ionization of the target. The photo-ionization leads to plasma formation, which is followed by electrostatic ejection of the target ions. The entire process of the ionization, plasma formation, and coulombic explosion must happen on a timescale shorter than the heat can diffuse beyond the volume of material being ablated.

Each pulse of the ultrafast laser removes a given amount of material faster than the heat generated can diffuse from that localized volume to the material nearby. Picosecond and nanosecond pulse lasers may initiate multi-photon ionization; however, the longer pulses allow the heat imparted by the laser to diffuse beyond the ablation volume and into the lattice surrounding the target. Heat diffusion into the metal creates thermal damage and changes to the microstructure such as Heat-Affected Zones (HAZ), melts areas, recast, slag, or dross. Scanning Electron Microscope (SEM), Energy-dispersive X-ray spectroscopy (EDX), and X-ray diffraction (XRD) may be used to assess microstructural changes, heat affected zones, recast, dross, or slag on the surface of the metal.

Figure 9E:
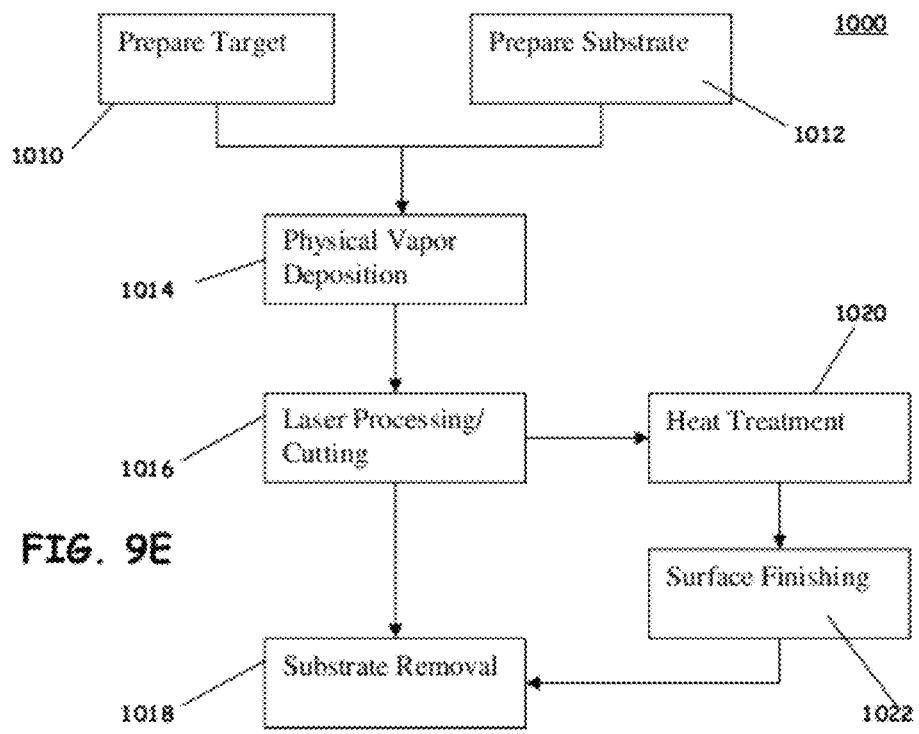
FIG. 9E is a flow chart of one embodiment for the method of manufacturing the stent.

As such, a diagram for laser machining the stent with thicknesses between about 5 and 75 microns may be achieved by femtosecond lasers. FIG. 9E shows a flow chart of the method of manufacturing the stent 1000, starting with step 1010 of preparing the target for deposition and step 1012 of preparing the substrate for deposition as indicated above. Step 1014 then proceeds with physical vapor deposition of the tubular stent structure or any other deposition technique described above. Then step 1016 proceeds with laser processing or machining the tubular stent structure. With femtosecond laser machining techniques as described above, the substrate may be removed in step 1018 for substrate removal without any post-processing steps. Such post-processing steps are heat treatment 1020 and surface finishing 1022.

EXAMPLE 1

A pattern design was cut into a vacuum deposited metallic stent in an unexpanded state having a wall thickness of about 50 μm using a femto-second laser. Referring to FIGS. 9A and 9B, the pattern design included pluralities of the first structural elements 310 connected by a plurality of the second structural elements 312, as described above. Use of the femto-second laser facilitated accurate and precise control of each of the dimensions, for example, 310c, 312a, 318, 320, 322, 324, 326, 330, and 332 illustrated in FIGS. 9A and 9B.

Such dimensions include, for example, widths 310c and 312a of the first and second structural elements 310 and 312, respectively, a length 318 of the first structural element 310 less a peak and trough, a peak-to-peak or trough-to-trough length 320 measured along the circumferential axis 314, a length 322 of a longitudinal interspacing between adjacent pluralities of the first structural elements 310, a length 324 measured longitudinally from a peak of a first one of the first structural elements to a peak of a second one of the first structural elements, wherein the first and second first structural elements 310 are disposed in pluralities of the first structural elements 310 separated by a plurality of the first structural elements 310, a peak or trough width 326, a length 330 of the stent 350, and a diameter 332 of the stent 350.

The aforementioned features were fabricated on the stent 350 in the unexpanded state. The above-noted dimensions had about the values indicated in Table 1 hereinbelow.

TABLE 1

Exemplary sizes of laser cut elements of the stent 350 in the unexpanded state

| Element of the stent 350 | Reference Number | Dimension (about)(μm) |
|---|---|---|
| Width of the first structural element 310 | 310c | 29 |
| Width of the second structural element 312 | 312a | 29 |
| Length of 310 less a peak and a trough | 318 | 368 |
| Peak to peak circumferential length | 320 | 118 |
| Longitudinal spacing between pluralities of 310 | 322 | 67 |

TABLE 1-continued

Exemplary sizes of laser cut elements of the stent 350 in the unexpanded state

| Element of the stent 350 | Reference Number | Dimension (about)(μm) |
|---|---|---|
| Peak to peak longitudinal spacing | 324 | 1056 |
| Width of peak or trough | 326 | 35 |
| Length of the stent 350 | 330 | 21000 |
| Diameter of the stent 350 | 332 | 4250 |

The intravascular stent pattern may be cut or machined in the unexpanded configuration followed by a post expansion to the intended diameter. Alternatively, the intravascular stent pattern may be cut or machined in the expanded state such that upon release from the substrate, the stent does not require further processing to achieve a target expanded diameter.

In accordance with one embodiment, the inner surface 301 of the stent 300 and the stent 350 (See FIG. 18) may be provided with at least one groove 400. If desired, as will be hereinafter described in greater detail, a plurality of grooves 400 could be provided on, or in, the inner surface 301 of the stent 300, 350. The use of the term "groove" throughout this specification and in the claims is intended to be construed as: a channel or depression; a notch or a V-shaped or rounded indentation; or a scratch, or a mark, having been made with something sharp or jagged. The at least one groove 400, or grooves, of one embodiment may be provided in, or on, the inner surface 301 of the stent 300 in any suitable manner, such as by: abrading the inner surface 301 to provide the at least one groove 400; a chemical or mechanical etching process; use of a laser or laser etching process; use of a diamond-tipped tool; use of any suitable abrasive material; or use of any tool or process, which can provide the desired groove, or grooves, 400 in, or on, the inner surface 301 of stent 300, 350, as will be hereinafter described in greater detail.

As shown in FIG. 8, the at least one groove, or grooves, 400 may be disposed with its longitudinal axis 410 being disposed substantially parallel with the longitudinal axis 305, 316 of the stent 300, 350, respectively. Alternatively, the longitudinal axis 410 of the at least one groove 400 may be disposed substantially perpendicular to the longitudinal axis 305, 316, as illustrated by groove 400""; or the longitudinal axis 410 of the groove may be disposed at an obtuse, or acute, angle with respect to the longitudinal axis 305, 316, as illustrated by groove 400'. The angle that the groove 400' makes with respect to longitudinal axis 305, 316 is either an acute or an obtuse angle dependent upon from which direction the angle is measured with respect to the longitudinal axis 305, 316. For example, if the angle between the longitudinal axis of the groove 400' and the longitudinal axis 305, 316 is measured as indicated by arrows A, the angle is an acute angle. If the angle is measured, as at arrows B, the angle is an obtuse angle.

Still with reference to FIG. 8, a plurality of the grooves 400 may be provided on the inner surface 301 of the stent 300, 350, two grooves 400 being shown for illustrative purposes only. Instead of a plurality of individual grooves, such as the grooves 400, a single groove 400" could be provided in a serpentine fashion, so as to cover as much of the inner surface 301 of the stent 300, 350 as desired. Similarly, the grooves could be provided in a cross-hatched manner, or pattern, as shown by the grooves 400"'. The grooves 400, 400', 400", 400"', and 400"" could be provided alone or in combination with each other, as desired, to provide whatever pattern of grooves is desired, including a symmetrical, or an asymmetrical, pattern of grooves. It should be noted that the angular disposition and location of the various grooves 400-400"" will vary and be altered upon the expansion of the stent 300, 350 within artery 290 (FIG. 1), the stent 300 being illustrated in its unexpanded configuration in FIG. 8. Similarly, if the stent 300, 350 were made of wire or lengths of wire, the disposition and angular orientation of the grooves formed on such wire, or wire members, would similarly be altered upon the expansion and implantation of such stent. It should be further noted, as previously discussed, that the groove, or grooves, may be provided in, or on, the inner surface of any intravascular stent, for example, the intravascular stent 300, 350, so as to increase the rate of migration of endothelial cells on, and over, the inner surface of the intravascular stent 300, 350.

With reference to FIGS. 10-17, various embodiments of the groove 400 will be described in greater detail. In general, as seen in FIG. 10, the groove 400 has a width W, a depth D, and a length L (See FIG. 8). The width W and depth D may be the same, and not vary, along the length L of the groove 400. Alternatively, the width W of the groove may vary along the length L of the groove 400. Alternatively, the depth D of the groove may vary along the length L of the at least one groove 400. Alternatively, both the width W and the depth D of the groove 400 may vary along the length of the at least one groove. Similarly, as with the location and angular disposition of the groove, or grooves, 400 as described in connection with FIG. 8, the width W, depth D, and length L of the groove, or grooves, 400 can vary as desired, and different types and patterns of the grooves 400 could be disposed on the inner surface 301 of the stent 300, 350.

As shown in FIGS. 10-17, the groove 400 may have a variety of different cross-sectional configurations. As desired, the cross-sectional configuration of the groove, or grooves, 400 may vary along the length L of the groove; or the cross-sectional configuration of the groove 400 may not vary along the length of the at least one groove 400. Similarly, combinations of such cross-sectional configurations for the grooves 400 could be utilized. The cross-sectional configuration of the groove, or grooves, 400 may be substantially symmetrical about the longitudinal axis 410 of the groove 400 as illustrated in FIGS. 8 and 10; or the cross-sectional configuration of the at least one groove 400 may be substantially asymmetrical about the longitudinal axis 410 of the least one groove 400, as illustrated in FIGS. 15 and 17. The cross-sectional configurations of the groove 400 can assume a variety of shapes, some of which are illustrated in FIGS. 10-17, and include those cross-sectional configurations which are substantially: square shaped (FIG. 10); U shaped (FIG. 11); triangular, or V shaped (FIG. 12); rectangular shaped (FIG. 13); and triangular, or keyway shaped (FIG. 14). Wall surface 303 of each groove 400 may be substantially smooth, such as illustrated in FIGS. 10-14, or the wall surface 303 may be jagged, or roughened, as illustrated in FIGS. 15 and 17. As illustrated in FIG. 16, the wall surface 303 could also be provided with at least one protrusion 304 and at least one indentation 306 if desired, and additional protrusions and indentations 304, 306 could be provided as desired.

The depth D of the groove, or grooves, 400 may fall within a range of approximately one-half to approximately ten microns. However, it is preferable that the depth D of the groove, or grooves, 400 not exceed the distance between the inner surface 301 and the outer surface 302 of the stent 300, 350. The width W of groove, or grooves, 400, may fall within a range of approximately two to approximately forty microns. Of course, the width W and depth D could be varied from the foregoing ranges, provided the rate of migration of endothelial cells onto the stent 300, 350 is not impaired. The length L of the groove 400 may extend the entire length of stent 300, 350, such as the groove 400 of FIG. 8; or the length L' of a groove may be less than the entire length of stent 300, such as the groove 400"" in FIG. 8. The groove, or grooves, 400 of one embodiment may be continuous, or discontinuous, along inner surface 301 of the stent 300, 350.

The portion of the inner surface 301 of the stent 300, 350 which has not been provided with a groove, or grooves, 400 in accordance with one embodiment, may have any suitable, or desired, surface finish, such as an electropolished surface, as is known in the art, or may be provided with whatever surface finish or coating is desired. It is believed that when at least one groove in accordance with one embodiment is disposed, or provided, on, or in, the inner surface 301 of the intravascular stent 300, 350, after the implantation of the stent 300, 350, the rate of migration of endothelial cells upon the inner surface 301 will be increased over that rate of migration which would be obtained if the inner surface 301 were not provided with the at least one groove 400 in accordance with one embodiment.

Figure 18:
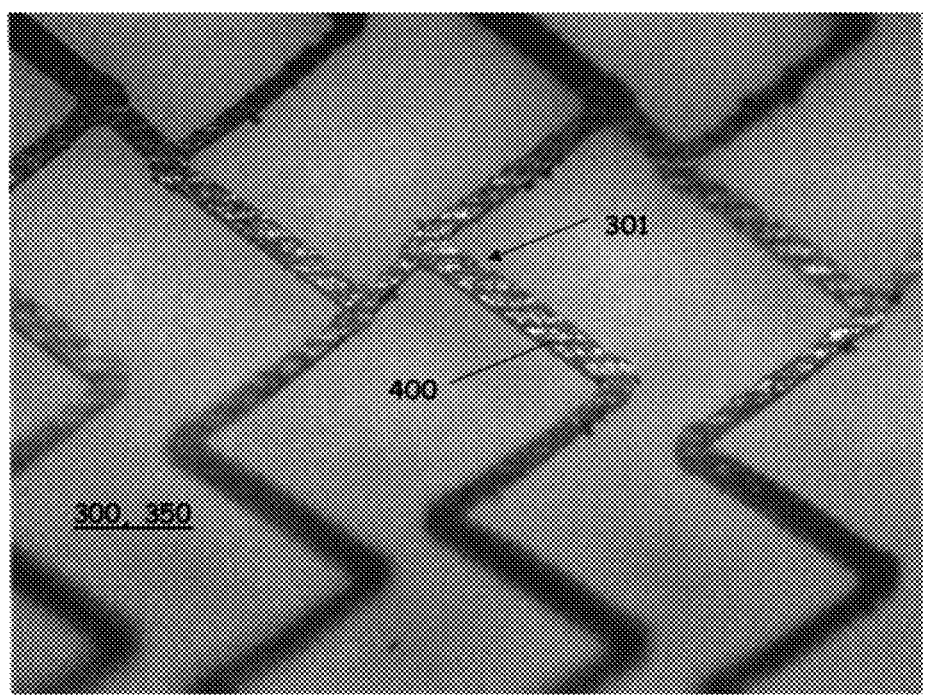
FIG. 18 is a plan view of an inner portion of an intravascular stent as released from the substrate in accordance with one embodiment.

With reference to FIG. 18, the inner surface 301 of the intravascular stent 300, 350 may be inscribed with a grooved pattern by pre-structuring the surface of a substrate onto which the deposition takes place. Etching, photolithography techniques, mechanical machining, and/or laser machining methods, as described hereinbelow with regard to FIGS. 25A-26B and 29, may be applied to the substrate surface to create a positive or negative image of a desired pattern. Subsequently, material may be vacuum deposited over the image of the desired pattern to create the inner surface 301 of the deposited material including the desired pattern.

Alternatively, a mask or a set of masks, which are either stationary or moveable relative to the substrate, may be used to define the pattern of at least one groove that is applied to the substrate. Patterning may be employed to achieve complex finished geometries of the resultant stent 300, 350, both in the context of spatial orientation of the pattern, as well as the material thickness at different regions of the deposited film, such as by varying the wall thickness of the material over its length to thicken sections at proximal or distal ends of the stent 300, 350 to prevent flaring of the stent upon radial expansion of the stent.

With reference to FIG. 19, a calendaring apparatus 450 is illustrated forming at least one groove 400 (not shown) on, or in, the inner surface 301 of stent blank 300. Calendaring apparatus 450 includes at least one calendaring roller 451 and an inner mandrel 452. Calendaring roller 451 is provided with a bearing shaft 453 and a pinion gear 454, which is driven by a gear drive 455 and gear drive apparatus 456. Bearing shaft 453 is received in a bearing block 457, which has a groove 458 for receipt of bearing shaft 453. Bearing block 457 also includes a bottom plate 459 and bearing block 457 is movable therein, in the direction shown by arrows 460, as by slidably mating with slots 461 formed in bottom plate 459. Bearing block 457 is further provided with an opening, or bearing journal, 465 for rotatably receiving mounting hub 466 disposed upon the end of mandrel 452. Calendaring roller 451 is rotated in the direction shown by arrow 467 and bears against the outer surface 302 of stent blank 300, with a force sufficient to impart the groove pattern 468 formed on the outer surface of mandrel 452 to the inner surface 301 of stent blank 300. Mandrel 452 will have a raised groove pattern 468 on the outer surface of mandrel 452, corresponding to the desired groove, or grooves, 400 to be formed on, or in, the inner surface 301 of stent 300. The raised groove pattern 468 of mandrel 452 must be hardened sufficiently to enable the formation of many stents 300 without dulling the groove pattern 468 of mandrel 452. Mandrel 452 may have a working length corresponding to the length of the stent 300 and an overall length longer than its working length, to permit the receipt of mandrel mounting hub 466' within bearing block 457 and mounting hub 466 within gear drive apparatus 456.

Still with reference to FIG. 19, the outer diameter of mandrel 452 is preferably equal to the inner diameter of the stent 300 in its collapsed state. The groove pattern 468 may correspond to the desired groove pattern of groove, or grooves, 400 to be formed on the inner surface 301 of stent 300 after stent 300 has been fully expanded. If the desired groove pattern upon expansion of stent 300 is to have the groove, or grooves 400 become parallel to each other upon expansion of the stent 300, along the longitudinal axis of the expanded stent 300, groove pattern 468, or the pre-expanded groove pattern, must have an orientation to obtain the desired post expansion groove pattern, after radial expansion of stent 300. Stent 300 may be pre-expanded slightly to facilitate its placement on the mandrel 452 in order to prevent scratching of the stent 300. Mandrel 452 may include an orientation mechanism, or pin 469 which mates with a corresponding notch 469' on stent blank 300, in order to insure proper orientation of stent blank 300 with respect to mandrel 452. Stent 300 may be crimped circumferentially around mandrel 452 after it has been properly oriented. The force to impart the desired groove pattern 468 upon, or in, the inner surface 301 of stent 300 is provided by calendaring roller 451.

With reference to FIG. 20, an alternative structure is provided to impart the desired groove pattern in, or upon, the inner surface 301 of stent blank 300. In lieu of calendaring roller 451, a punch press, or stamping apparatus, 470 may be utilized to force the inner surface 301 of stent 300 upon the groove pattern 468 of mandrel 452. Stamping apparatus 470 may include a hydraulic cylinder 471 and hydraulic piston 472, attached to a stamping segment 473. The inner surface 474 of stamping segment 473 has a radius of curvature which matches the outer radius of curvature 475 of stent 300, when it is disposed upon mandrel 452. If desired, a plurality of stamping devices 470' may be disposed about the outer surface 302 of stent 300, or alternatively a single stamping device 470 may be utilized, and stent 300 and mandrel 452 may be rotated to orient the stent 300 beneath the stamping segment 473.

Figure 21:
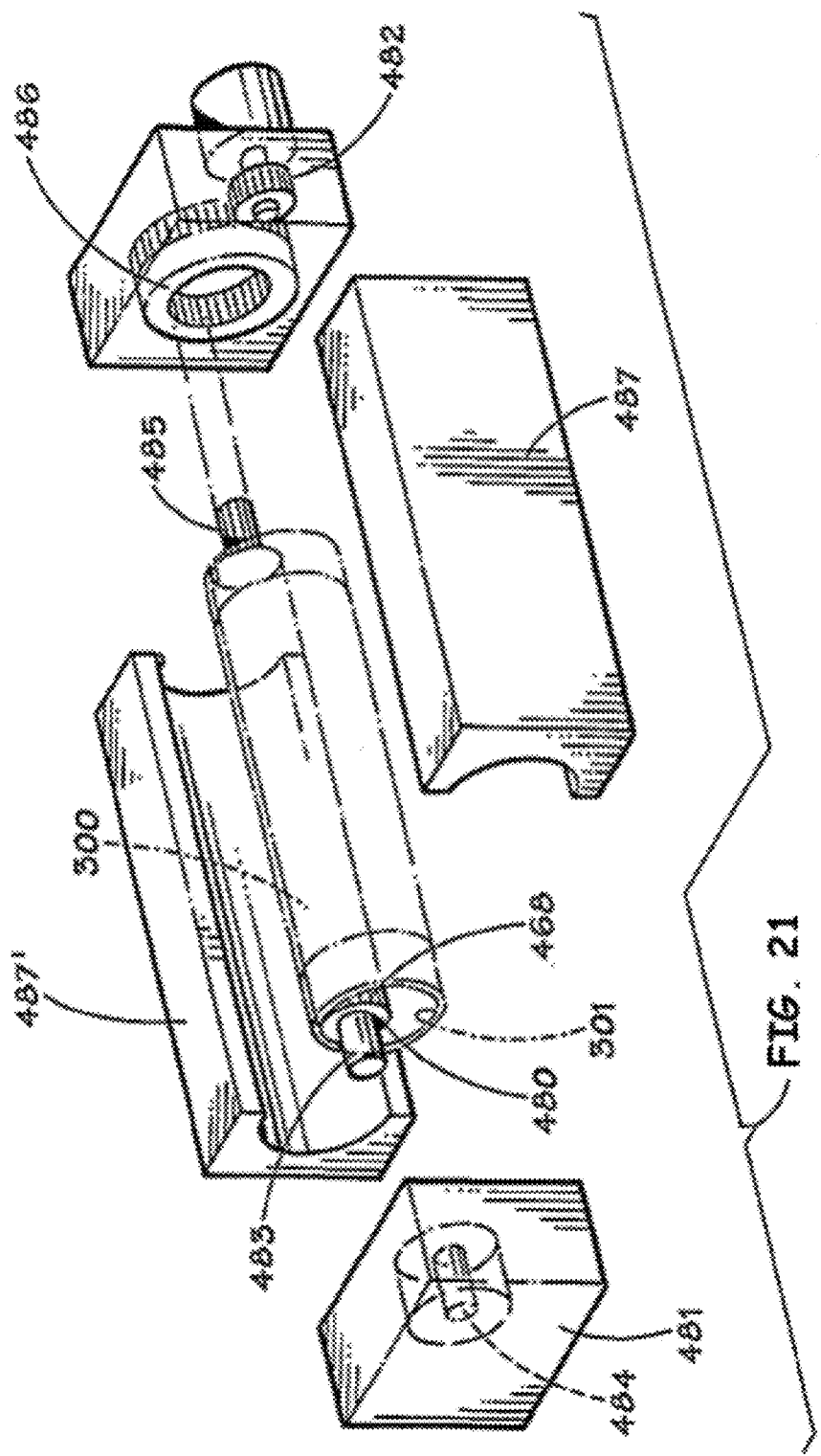
FIG. 21 is an exploded perspective view of an apparatus utilizing an impression roller to manufacturer stents in accordance with one embodiment.

With reference to FIG. 21, the desired grooves 400 may be formed on the inner surface 301 of stent blank 300 by an impression roller 480 which serves as the inner mandrel. Impression roller 480 is supported at its ends by roller bearing block 481, similar in construction to previously described bearing block 457. Similarly, a gear drive, or drive gear mechanism, 482 may be provided, which is also similar in construction to gear drive 455. Impression roller 480 has a bearing shaft 483 at one end of impression roller 480, bearing shaft 483 being received by an opening, or journal bearing, 484 in bearing block 481. The other end of impression roller 480 may have a pinion gear 485 which is received within rotating ring gear 486 in gear drive mechanism 482. A backup housing, such as a two-part backup housing 487, 487' may be provided for fixedly securing stent blank 300 while impression roller 480 is rotated within stent blank 300 to impart groove pattern 468 formed on the exterior of impression roller 480 to the inner surface 301 of stent blank 300.

Figures 22, 23:
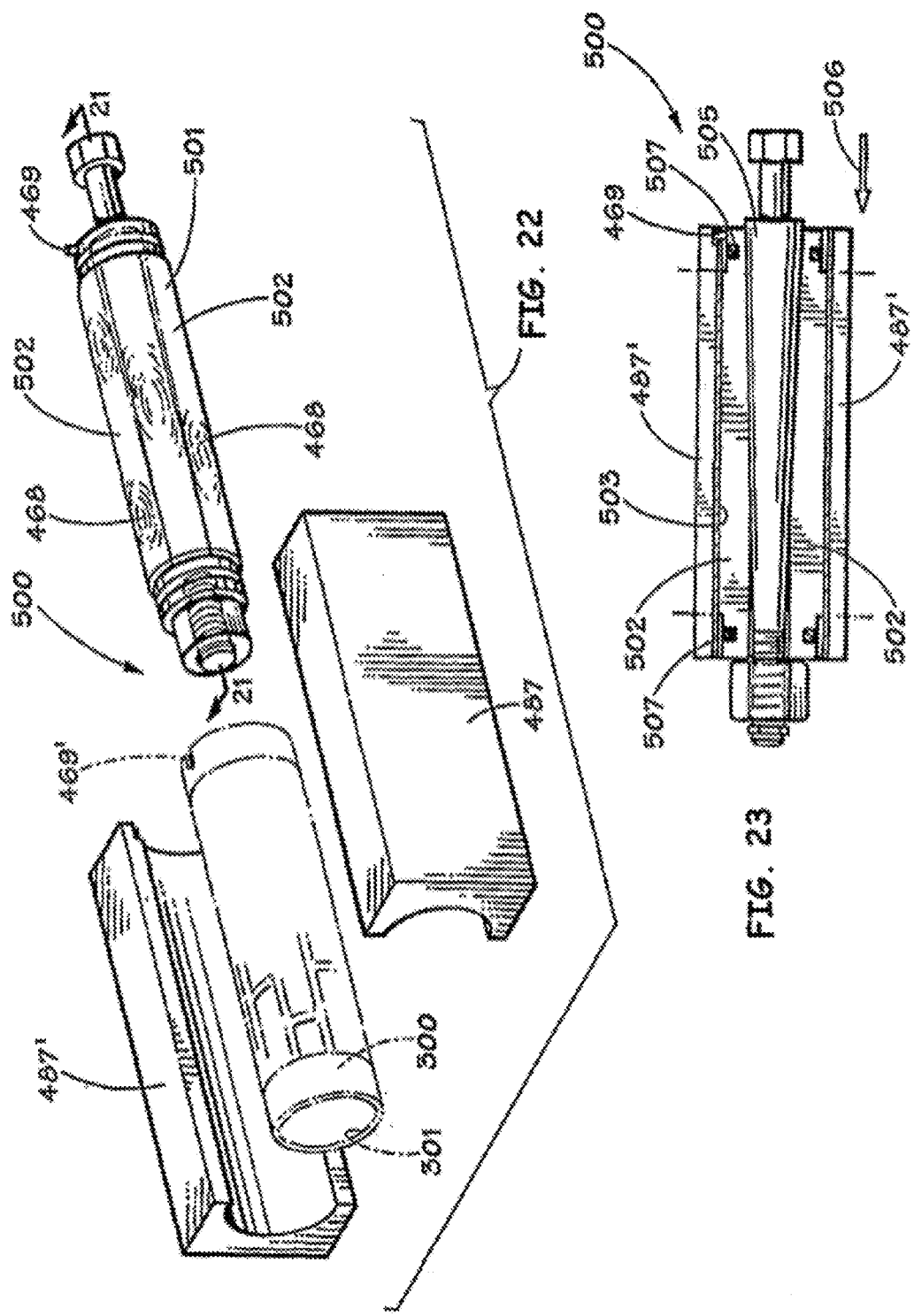
FIG. 22 is an exploded perspective view of an expanding mandrel apparatus for manufacturing stents in accordance with one embodiment.
FIG. 23 is a partial cross-sectional view of the mandrel of FIG. 22, taken along lines 21-21 of FIG. 22.

With reference to FIGS. 22 and 23, an expanding mandrel apparatus 500 for forming the desired at least one groove 400 on, or in, the inner surface 301 of stent blank 300 is illustrated. Expanding mandrel 501 is preferably formed of a plurality of mating and tapered segments 502 having the desired groove pattern 468 formed on the outer surface 503 of each segment 502. Stent blank 300 is disposed upon expanding mandrel 501 in the unexpanded configuration of expanding mandrel 501, stent blank 300 being oriented with respect to mandrel 501, as by the previously described notch 469' and pin 469. A backup housing 487 and 487', as previously described in connection with FIG. 21, may be utilized to retain stent blank 300 while expanding mandrel 501 is expanded outwardly to impart the desired groove pattern 468 upon, or in, the inner surface 301 of stent blank 300. In this regard, expanding mandrel 501 is provided with a tapered interior piston 505, which upon movement in the direction of arrow 506 forces mandrel segments 502 outwardly to assume their desired expanded configuration, which forces groove pattern 468 on mandrel 501 against the inner surface 301 of stent blank 300. O-rings 507 may be utilized to secure stent 300 upon mandrel 501.

Figure 24:
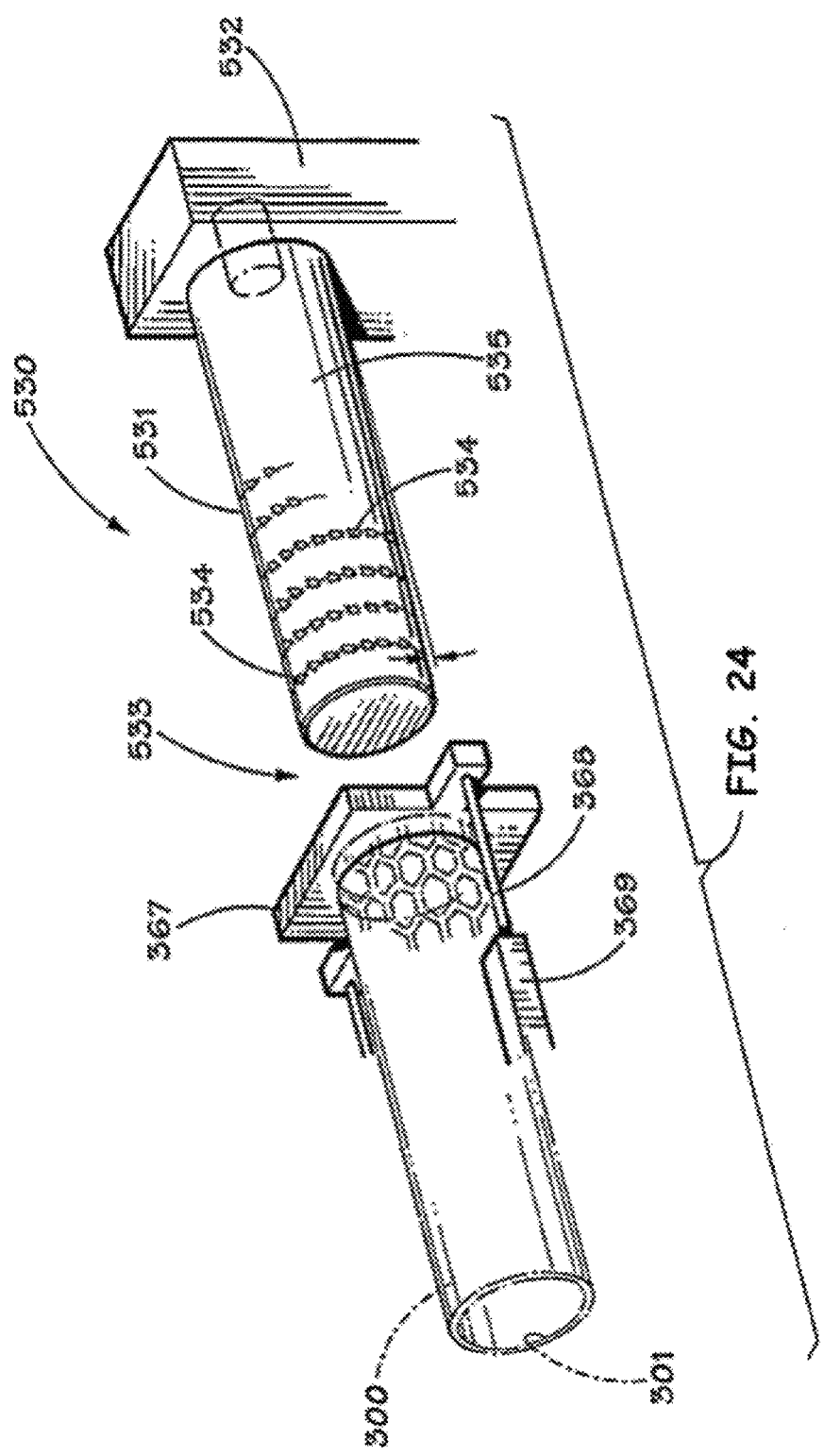
FIG. 24 is an exploded perspective view of an apparatus utilizing a tapered mandrel to manufacture stents in accordance with one embodiment.
Figure 25:
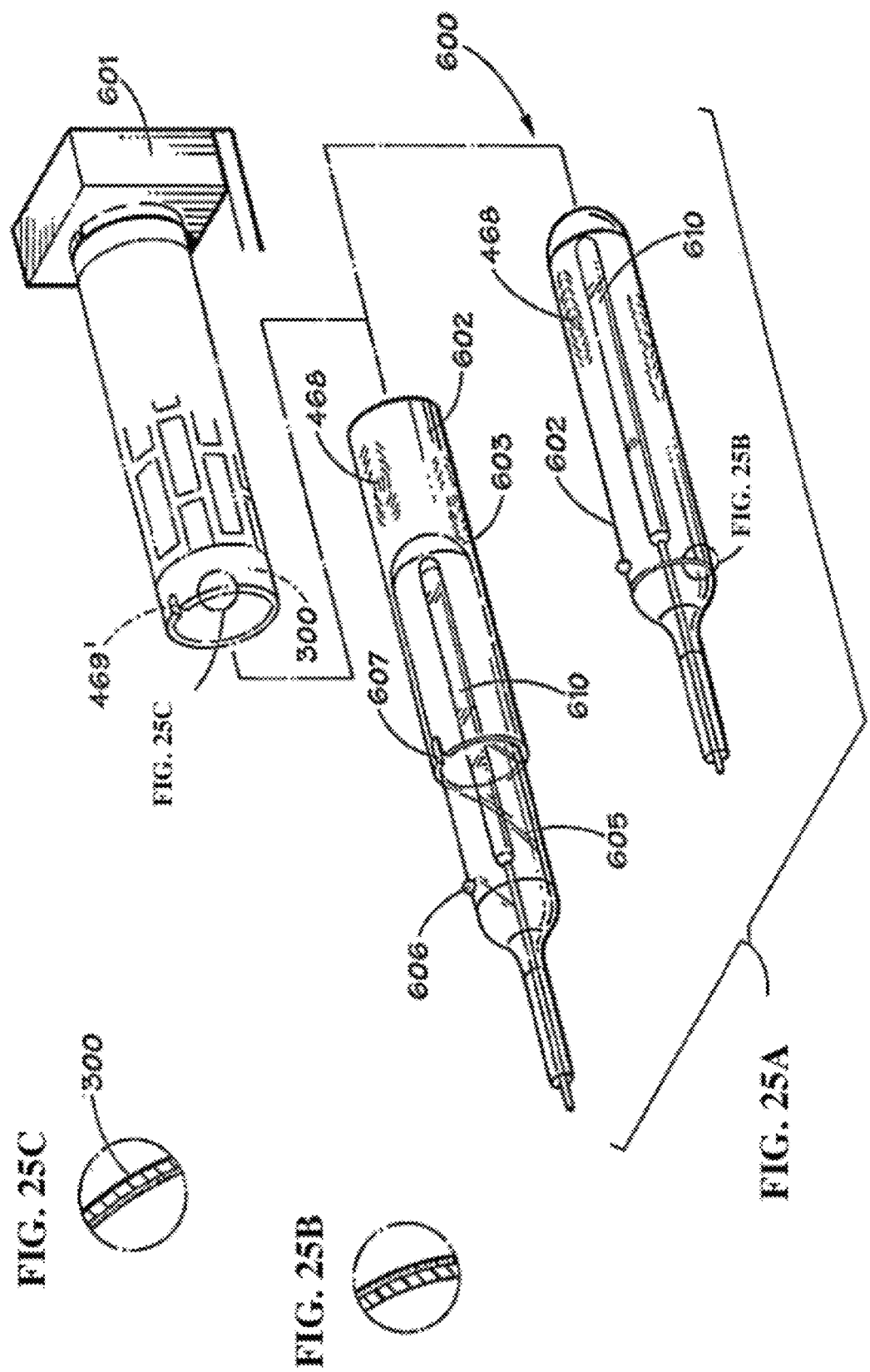
FIG. 25A is an exploded perspective view of an apparatus utilizing a chemical removal method to manufacture stents in accordance with one embodiment.
FIG. 25B illustrates an embodiment of a portion of the apparatus of FIG. 25A.
FIG. 25C illustrates another embodiment of a portion of the apparatus of FIG. 25A.
Figure 26:
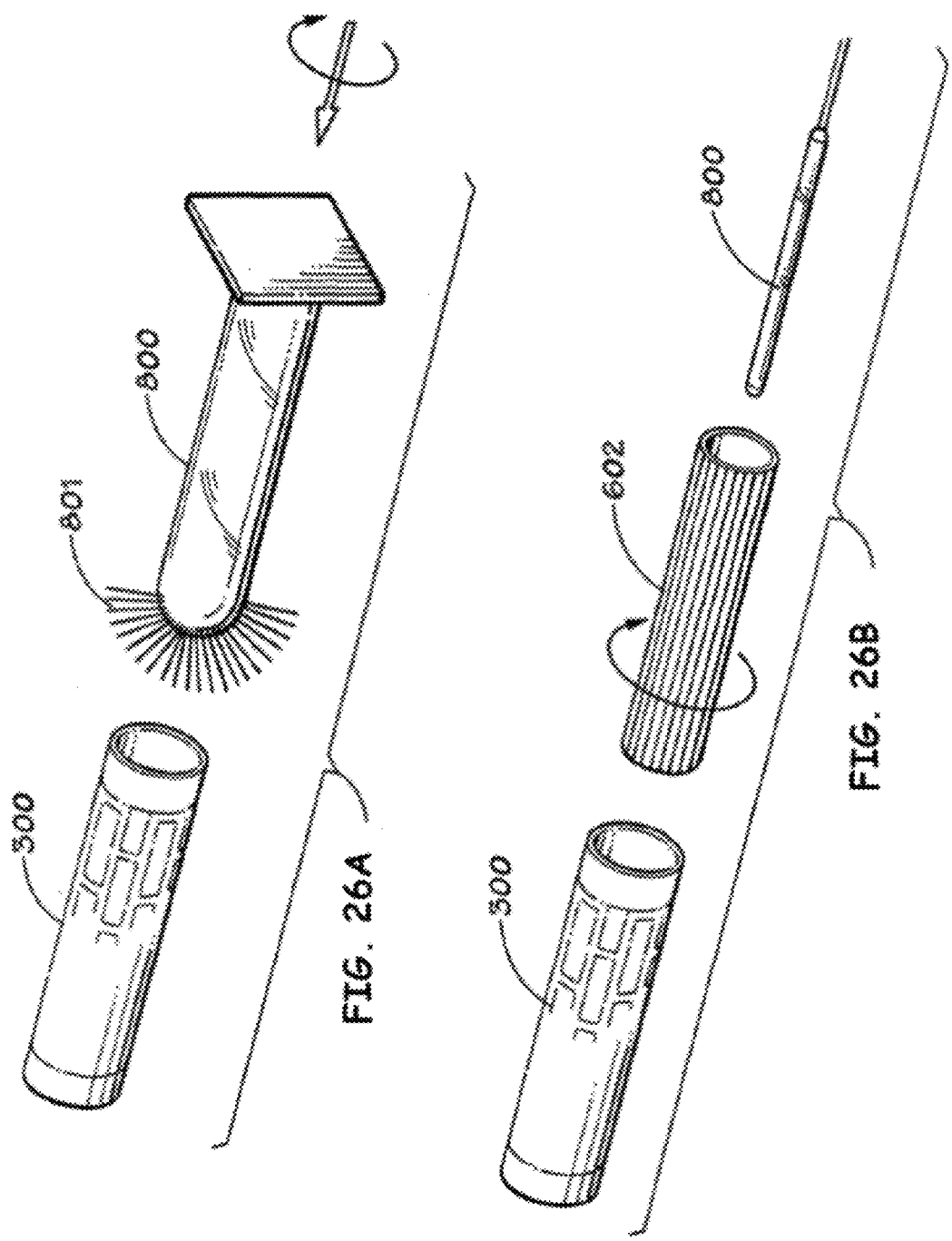
FIG. 26A is an exploded perspective view of an apparatus utilizing a rotating coaxial light source to inscribe microgrooves inside an intact tubular stent in accordance with one embodiment.
FIG. 26B is an exploded perspective view of an apparatus utilizing a rotating mask and fixed light source to inscribe microgrooves inside an intact tubular stent in accordance with one embodiment.

With reference to FIG. 24, a tapered mandrel groove forming apparatus 530 is illustrated. Tapered mandrel 531 is supported by a mandrel support bracket, or other suitable structure, 532 to fixedly secure tapered mandrel 531 as shown in FIG. 24. The end 533 of tapered mandrel 531, has a plurality of cutting teeth 534 disposed thereon. The cutting teeth 534 may be abrasive particles, such as diamond chips, or tungsten carbide particles or chips, which are secured to tapered mandrel 531 in any suitable manner, and the cutting teeth 534 form the desired groove, or grooves, 400 on, or in, the inner surface 301 of stent blank 300. Alternatively, instead of cutting teeth 534, the outer surface 535 of tapered mandrel 531 could be provided with a surface comparable to that formed on a metal cutting file or rasp, and the file, or rasp, profile would form the desired grooves 400. A stent holding fixture 367 is provided to support stent blank 300 in any desired manner, and the stent holding fixture 367 may be provided with a piston cylinder mechanism, 368, 369 to provide relative movement of stent 300 with respect to tapered mandrel 531. Alternatively, stent 300 can be fixed, and a suitable mechanism can be provided to move tapered mandrel 531 into and along the inner surface 301 of stent 300. Preferably, stent 300 is in its expanded configuration.

With reference to FIGS. 25A, 25B and 25C, a photolithographic method and apparatus 600 for forming the desired groove, or grooves, 400 on, or in, the interior surface 301 of stent blank 300 is illustrated. A stent holding fixture 601 is provided, and holding fixture 601 may be similar in construction to that of stent holding fixture 367 of FIG. 24. Again, stent blank 300 is provided with an orientation notch, or locator slot, 469'. A photo mask 602 is formed from a material such as Mylar film. The dimensions of the mask, 602 correspond to the inner surface area of the inner surface 301 of stent 300. The mask 602 is formed into a cylindrical orientation to form a mask sleeve 603, which is wrapped onto a deflated balloon 605, such as a balloon of a conventional balloon angioplasty catheter. A conventional photoresist material is spin coated onto the inner surface 301 of stent blank 300. The mask sleeve 603, disposed upon balloon 605 is inserted into stent 300, and balloon 605 is expanded to force the mask sleeve 603 into an abutting relationship with the photoresist coated inner surface 301 of stent 300. Balloon 605 may be provided with an orientation pin 606 which corresponds with an orientation notch 607 on mask sleeve 603, which in turn is also aligned with locator slot 469' on stent blank 300. The expansion of balloon 605 is sufficient to sandwich mask sleeve 603 into abutting contact with the photoresist coated inner surface 301 of stent 300; however, the balloon 605 is not inflated enough to squeeze the photoresist material off the stent 300. The interior surface 301 of stent 300 is then irradiated through the inside of the balloon 605 through the balloon wall, as by a suitable light source 610. Balloon 605 is then deflated and mask sleeve 603 is removed from the interior of stent 300. The non-polymerized photoresist material is rinsed off and the polymerized resist material is hard baked upon the interior of stent 300. The groove, or grooves 400 are then chemically etched into the non-protected metal surface on the interior surface 301 of stent 300. The baked photoresist material is then removed by either conventional chemical or mechanical techniques.

Alternatively, instead of using a Mylar sheet as a mask 602 to form mask sleeve 603, mask 602 may be formed directly upon the outer surface of balloon 605, as shown in FIG. 25B. The production of mask 602 directly upon the balloon outer surface can be accomplished by physically adhering the mask 602 onto the outer surface of balloon 605, or by forming the mask 602 onto the surface of balloon 605 by deposition of the desired groove pattern 468 by deposition of UV absorbing material by thin film methods. In the case of utilizing mask sleeve 603 as shown in FIG. 25C, the balloon material must be compliant enough so as to prevent creases from the balloon wall which may shadow the resulting mask 602. In the case of mask 602 being formed on balloon 605 as shown in FIG. 25B, a non-compliant balloon 605 should be used, so as not to distort the resulting image by the stretching of the compliant balloon wall. If on the other hand, the mask 602 is physically adhered to the outer wall of balloon 605, a compliant balloon 605 may be used provided the mask 602 is adhered to the balloon 605 when the balloon 605 is in its fully expanded diameter.

With reference to FIGS. 26A and 26B, a method is shown for creating grooves inside an intact tubular stent 300, which involves casting patterned light inside a stent 300 previously coated with photosensitive material as discussed, for example, in connection with FIG. 25A (PSM). The light exposed areas are subjected to chemical etching to produce the grooved pattern. This method involves using a coaxial light source 800 with multiple small beams 801 of light in a single plane. The light source 800 could be displaced along the longitudinal axis of the tube, or stent 300, at a rate consistent with adequate exposure of the photosensitive material. Computer driven stepper motors could be utilized to drive the light source longitudinally and/or radially, which would allow for interlacing grooves (see FIG. 26A). One pass could create 1 mm spacing, while the next pass creates 500 µm, and so on.

Rotational movements could introduce variability in the groove direction for zig-zag, spiral or undulating patterns. Alternatively, the light source 800 could be fixed as shown in FIG. 26B, and the beams would be as narrow and long as the grooves needed on the inner surface of the mask 602. Stepping of the mask 602 would allow narrow spacing of the grooves.

Figure 27:
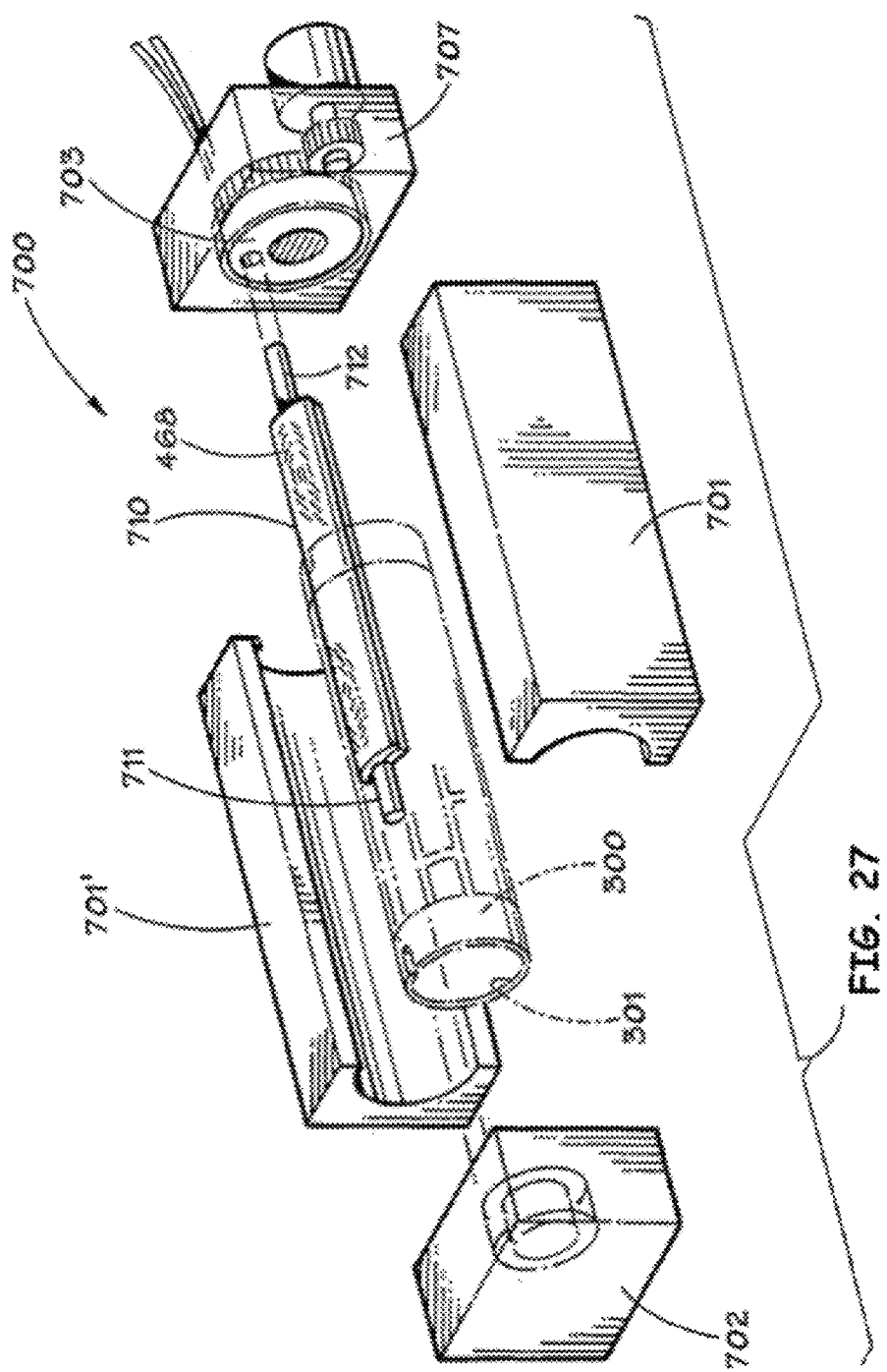
FIG. 27 is an exploded perspective view of an electric discharge machining apparatus for manufacturing stents in accordance with one embodiment.

With reference to FIG. 27, an EDM process and apparatus 700 provide the desired groove, or grooves, 400 upon the interior 301 of stent 300. A non-conductive stent alignment and holding fixture 701, 701', similar in construction to backup housings 487, 487', previously described, are provided for holding stent like blank 300. A bearing block assembly 702, similar to bearing block assembly 481 of FIG. 21, is provided along with an indexing and current transfer disk 703 provided within a drive gear mechanism 707, which is similar in construction to drive gear mechanisms 482 and 455, previously described in connection with FIGS. 21 and 19. An electric discharge machining ("EDM") electrode 710 having bearing shafts 711, 712, disposed at its ends, for cooperation with bearing block assembly 702 and disk 703, respectively, is rotated within stent blank 300. Current is provided to the raised surfaces, or groove pattern, 468, of electrode 710 to cut the desired groove, or grooves 400 into the inner surface 301 of stent 300.

Figure 28:
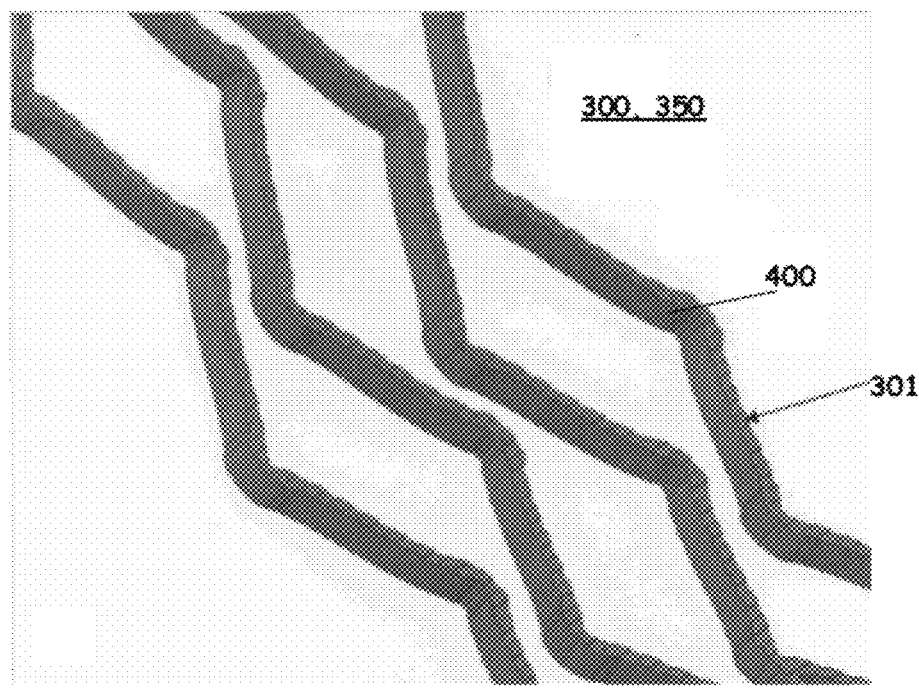
FIG. 28 is a plan view of an interior portion of an intravascular stent in accordance with one embodiment.

With reference to FIG. 28, in one embodiment, a laser machining process provides the desired groove, or grooves, 400 upon the inner surface 301 of the stent 300, 350. In this embodiment of the laser machining process, the intravascular stent 300, 350 is held by a pneumatically controlled 3C collet system. A femto-second laser is preferably used to provide the at least one groove, or grooves, 400 on the stent 300, 350.

Figure 29:
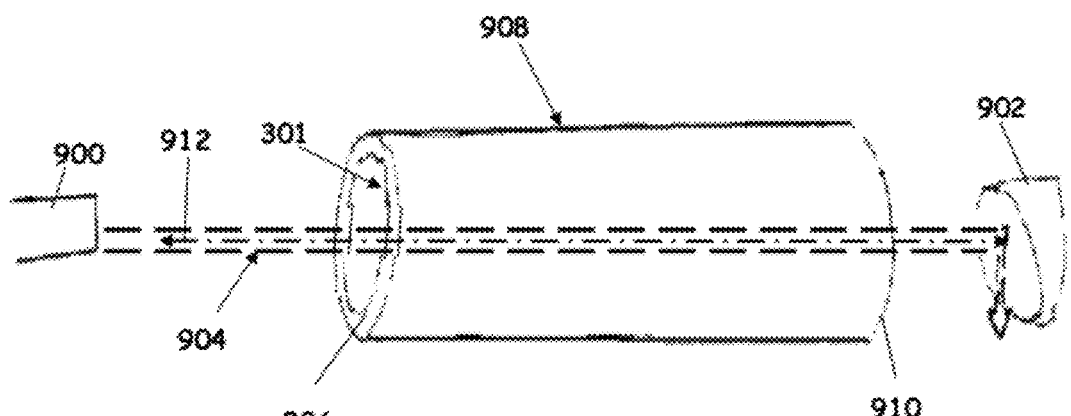
FIG. 29 is an exploded perspective view of an apparatus utilizing a laser and a mirror/prism to inscribe microgrooves inside an intact tubular stent in accordance with one embodiment.

With reference to FIG. 29, in another embodiment of a laser machining process, a laser 900 and mirror/prism 902 system provides the desired at least one groove, or grooves, 400 upon the inner surface 301 of the stent 300, 350. In this embodiment, a non-conductive stent alignment and holding fixture, similar in construction to backup housings 487 previously described in regard to FIGS. 21-23 and 27, is provided for holding stent like blank 908. The laser 900 is positioned at a proximal end 906 of the blank 908 such that a laser beam 904 is directed, along a longitudinal axis 912 of the blank 908, through the inner diameter of the blank 908. The mirror/prism 902 is positioned at a distal end 910 of the blank 908. The laser 900 is aligned with the mirror/prism 902 in order to redirect the laser beam 904 to cut at about 90° from the longitudinal axis 912 of the blank 908 so that the laser beam 904 is focused on the inner surface 301 of the blank 908.

In one embodiment, the blank 908 may be stationary and patterned with at least one groove, or grooves, 400 by having the mirror/prism 902 move linearly along the longitudinal axis 912 and/or rotate circumferentially about the longitudinal axis 912. The mirror/prism 902 could be displaced along the longitudinal axis 912 of the blank 908 at a rate suitable for adequate exposure of the inner surface 301 to the laser beam 904. Computer driven stepper motors could be utilized to drive the mirror/prism axially along and radially perpendicular to the longitudinal axis 912 of the blank 908, which could allow for interlacing grooves. One pass could create 1 mm spacing, while the next pass creates 500 µm, and so on.

In another embodiment, the blank 908 can be staged on a programmable linear slide with rotational (also programmable) capability. In this embodiment, with controlled slide and rotation, the blank 908 can be moved along the longitudinal axis 912 over the mirror/prism 902 and rotated around the mirror/prism 902 in order to create the desired at least one groove, or grooves, 400 on the inner surface 301 of the blank 908. Computer driven stepper motors could be utilized to drive the blank 908 axially along and radially perpendicular to the longitudinal axis 912 of the blank 908. Rotational movements could introduce variability in the groove direction for zig-zag, spiral, or undulating patterns.

Improved methods for creating a design pattern for a stent and for creating a pattern of grooves on an inner surface of the stent are presented. The methods include etching, photolithography techniques, mechanical machining, and laser machining A femto-second laser method can produce a design pattern with high dimensional accuracy and precision in a vacuum deposited metallic stent having a wall thickness in the range of about 5 to about 75 µm, alternatively, between about 10 to about 60 µm.

While the present invention has been described with reference to its preferred embodiments, those of ordinary skill in the art will understand and appreciate that variations in materials, dimensions, geometries, and fabrication methods may be or become known in the art, yet still remain within the scope of the present invention which is limited only by the claims appended hereto. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the endoluminal implantable surface, stent, or grafts described herein and to teach the best mode of carrying out the same.

What is claimed is:

1. A method of manufacturing a self-supporting endoluminal implantable surface, stent, or graft, the method comprising the steps of:
   a. providing a self-supporting endoluminal implantable surface, stent, or graft having an inner wall surface and an outer wall surface;
   b. forming a pattern design into the self-supporting endoluminal implantable surface, stent, or graft;
   c. pre-structuring at least one of the inner wall and the outer wall surfaces by applying an athermal ablation laser machining method to the at least one wall surface to create thereon an image of a desired pattern without heat affected zones; and
   d. vacuum depositing material over the image of the desired pattern on the at least one wall surface to create a patterned surface overlying the at least one wall surface and including the desired pattern;
   e. wherein a maximum wall thickness including the patterned surface overlying the at least one wall surface measures between about 10 and about 60 microns, wherein the self-supporting endoluminal implantable surface, stent, or graft has a smooth surface finish.

2. The method of claim 1, wherein the pre-structuring and vacuum depositing steps are applied to both of the inner wall and the outer wall surfaces such that the maximum wall thickness including patterned surfaces on each of the inner wall and outer wall surfaces measures between about 10 and about 60 microns.

3. The method of claim 1, wherein the athermal ablation laser machining method is selected from the group consisting of: a femto-second laser, an excimer laser, a water assisted laser, and laser assisted chemical machining.

4. The method of claim 1, wherein the forming step further comprises applying an athermal ablation laser machining method selected from the group consisting of: a femto-second laser, an excimer laser, a water assisted laser, and laser assisted chemical machining to form the pattern design.

5. The method of claim 1, wherein the forming step further comprises applying a photolithographic method to form the pattern design.

6. The method of claim 5, wherein the photolithographic method includes the steps of:

a. coating a surface of the self-supporting endoluminal implantable surface, stent, or graft with a photosensitive material;
   b. attaching a mask over the surface coated with the photosensitive material;
   c. irradiating the surface with a light source;
   d. removing the mask from the surface; and
   e. chemically etching the surface to form the pattern design.

7. The method of claim 6, wherein the light source is a coaxial light source with multiple beams of light in a single plane.

8. The method of claim 6, wherein the irradiating step further includes irradiating the surface with a light source, wherein the light source and the surface are at least one of displaced and rotated relative to one another during the irradiating step.

9. A method of manufacturing a self-supporting endoluminal implantable surface, stent, or graft, the method comprising the steps of:
   a. providing a self-supporting endoluminal implantable surface, stent, or graft having an inner wall surface and an outer wall surface;
   b. forming a pattern design into the self-supporting endoluminal implantable surface, stent, or graft by applying a first photolithographic method;
   c. pre-structuring at least one of the inner wall and the outer wall surfaces by applying a photolithographic method to the at least one wall surface to create an image of a desired pattern; and
   d. vacuum depositing material over the image of the desired pattern on the at least one wall surface to create a patterned surface overlying the at least one wall surface and including the desired pattern;
   e. wherein a maximum wall thickness including the patterned surface overlying the at least one wall surface measures between about 10 and about 60 microns, wherein the self-supporting endoluminal implantable surface, stent, or graft has a smooth surface finish.

10. The method of claim 9, wherein the pre-structuring and vacuum depositing steps are applied to both of the inner wall and the outer wall surfaces such that the maximum wall thickness including patterned surfaces on each of the inner wall and outer wall surfaces measures between about 10 and about 60 microns.

11. The method of claim 9, wherein the forming step further comprises applying an athermal ablation laser machining method selected from the group consisting of: a femto-second laser, an excimer laser, a water assisted laser, and laser assisted chemical machining to form the pattern design.

12. The method of claim 9, wherein the forming step further comprises applying a second photolithographic method to form the pattern design.

* * * * *